US011666651B2

(12) United States Patent
Brander et al.

(10) Patent No.: US 11,666,651 B2
(45) Date of Patent: Jun. 6, 2023

(54) PRIME/BOOST IMMUNIZATION REGIMEN AGAINST HIV-1 UTILIZING A MULTIEPITOPE T CELL IMMUNOGEN COMPRISING GAG, POL, VIF, AND NEF EPITOPES

(71) Applicant: AELIX THERAPEUTICS, S.L., Barcelona (ES)

(72) Inventors: Christian Brander, Tiana (ES); Beatriz Mothe-Pujadas, Tiana (ES)

(73) Assignee: AELIX Therapeutics, S.L., Barcelona (ES)

(*) Notice: Subject to any disclaimer, the term of this patent is extended or adjusted under 35 U.S.C. 154(b) by 136 days.

(21) Appl. No.: 17/096,397

(22) Filed: Nov. 12, 2020

(65) Prior Publication Data

US 2021/0145961 A1 May 20, 2021

Related U.S. Application Data

(60) Provisional application No. 62/935,519, filed on Nov. 14, 2019.

(51) Int. Cl.
*A61K 39/21* (2006.01)
*A61P 31/18* (2006.01)
*A61K 45/06* (2006.01)
*A61K 39/00* (2006.01)

(52) U.S. Cl.
CPC .............. *A61K 39/21* (2013.01); *A61K 45/06* (2013.01); *A61P 31/18* (2018.01); *A61K 2039/5256* (2013.01); *A61K 2039/545* (2013.01); *C12N 2710/10034* (2013.01); *C12N 2710/10043* (2013.01); *C12N 2710/24034* (2013.01); *C12N 2710/24043* (2013.01); *C12N 2740/16034* (2013.01)

(58) Field of Classification Search
CPC ..................................................... A61K 39/21
See application file for complete search history.

(56) References Cited

U.S. PATENT DOCUMENTS

| | | |
|---|---|---|
| 5,081,226 A | 1/1992 | Berzofsky et al. |
| 5,128,319 A | 7/1992 | Arlinghaus |
| 5,554,372 A | 9/1996 | Hunter |
| 5,639,854 A | 6/1997 | Sia et al. |
| 5,700,635 A | 12/1997 | Mcmichael et al. |
| 5,759,769 A | 6/1998 | Sia et al. |
| 5,795,955 A | 8/1998 | Sia et al. |
| 5,800,822 A | 9/1998 | Sia et al. |
| 5,817,754 A | 10/1998 | Sia et al. |
| 5,876,731 A | 3/1999 | Sia et al. |
| 5,951,986 A | 9/1999 | Sia et al. |
| 5,972,339 A | 10/1999 | Walker |
| 5,976,541 A | 11/1999 | Berzofsky et al. |
| 6,093,400 A | 7/2000 | Zimmerman et al. |
| 6,111,068 A | 8/2000 | Zimmerman et al. |
| 6,174,666 B1 | 1/2001 | Pavlakis et al. |
| 6,210,873 B1 | 4/2001 | Sastry et al. |
| 6,265,539 B1 | 7/2001 | Arlinghaus et al. |
| 6,268,472 B1 | 7/2001 | Zimmerman et al. |
| 6,268,945 B1 | 7/2001 | Zimmermann et al. |
| 6,294,322 B1 | 9/2001 | Berzofsky et al. |
| 6,440,422 B1 | 8/2002 | Sutter et al. |
| 7,094,405 B1 | 8/2006 | Berzofsky et al. |
| 7,094,408 B2 | 8/2006 | Franchini et al. |
| 7,319,000 B1 | 1/2008 | Sastry et al. |
| 7,569,228 B2 | 8/2009 | Howley et al. |
| 7,612,173 B2 | 11/2009 | Abrecht et al. |
| 7,815,916 B1 | 10/2010 | Chang et al. |
| 7,820,786 B2 | 10/2010 | Thomson et al. |
| 7,981,430 B2 | 7/2011 | Hanke et al. |
| 7,993,651 B2 | 8/2011 | Hanke et al. |
| 8,000,900 B2 | 8/2011 | Heckerman et al. |
| 8,021,669 B2 | 9/2011 | Howley et al. |
| 8,143,054 B2 | 3/2012 | Howley et al. |
| 8,198,082 B2 | 8/2012 | Hitchman et al. |
| 8,309,098 B2 | 11/2012 | Howley et al. |
| 8,478,535 B2 | 7/2013 | Jojic et al. |
| 9,017,691 B2 | 4/2015 | Barouch et al. |
| 9,133,478 B2 | 9/2015 | Moss et al. |
| 9,133,480 B2 | 9/2015 | Moss et al. |
| 9,714,435 B2 | 7/2017 | Douglas et al. |
| 9,988,425 B2 | 6/2018 | Brander et al. |
| 10,815,278 B2 | 10/2020 | Brander et al. |
| 11,325,946 B2 | 5/2022 | Brander et al. |
| 2002/0151678 A1 | 10/2002 | Arlinghaus |
| 2003/0108562 A1 | 6/2003 | Hanke et al. |

(Continued)

FOREIGN PATENT DOCUMENTS

| | | |
|---|---|---|
| CH | 568392 | 10/1975 |
| EP | 1312678 A1 | 5/2003 |

(Continued)

OTHER PUBLICATIONS

Von Schwedler, U. K., et al., May 2003, Functional surfaces of the human immunodeficiency virus type 1 capsid protein, J. Virol. 77(9):5439-5450.*

Melamed, D., et al., Sep. 2004, The conserved carboxy terminus of the capsid domain of huma immunodeficiency virus type 1 Gag protein is important for virion assembly and release, J. Virol. 78(18):9675-9688.*

Fackler, O. T., et al., 2006, Functional characterization of HIV-1 Nef mutants in the context of viral infection, Virol. 351:322-339.*

Xiao, Z., et al., 2007, Characterization of a novel Cullin5 binding domain in HIV-1 Vif, J. Mol. Biol. 373:541-550.*

Greenspan, N. S., Jul. 2014, Design challenges for HIV-1 vaccines based on humoral immunity, Front. Immunol. 5:Article 355, pp. 1-3.*

(Continued)

*Primary Examiner* — Jeffrey S Parkin
(74) *Attorney, Agent, or Firm* — Sterne, Kessler, Goldstein & Fox P.L.L.C.

(57) ABSTRACT

The present invention relates to immunogenic therapies for the treatment or prevention of a human immunodeficiency virus (HIV) infection or a disease associated with an HIV infection.

32 Claims, 2 Drawing Sheets

Specification includes a Sequence Listing.

(56) References Cited

U.S. PATENT DOCUMENTS

| | | |
|---|---|---|
| 2003/0138409 A1 | 7/2003 | Pancre et al. |
| 2004/0073008 A1 | 4/2004 | Iglesias et al. |
| 2004/0105871 A1 | 6/2004 | Robinson et al. |
| 2004/0106136 A1 | 6/2004 | Dong |
| 2005/0249742 A1 | 11/2005 | Ruprecht et al. |
| 2006/0095241 A1 | 5/2006 | Jojic et al. |
| 2006/0160070 A1 | 7/2006 | Mallal et al. |
| 2006/0190226 A1 | 8/2006 | Jojic et al. |
| 2006/0257865 A1 | 11/2006 | Mallal |
| 2007/0015721 A1 | 1/2007 | Beaton et al. |
| 2007/0048861 A1 | 3/2007 | Robinson et al. |
| 2007/0248584 A1 | 10/2007 | Kent |
| 2008/0306244 A1 | 12/2008 | Hanke et al. |
| 2009/0060947 A1 | 3/2009 | Tartaglia et al. |
| 2009/0203144 A1 | 8/2009 | Beaton et al. |
| 2009/0252754 A1 | 10/2009 | Caputo et al. |
| 2010/0055119 A1 | 3/2010 | Stoloff et al. |
| 2010/0088037 A1 | 4/2010 | Mallal |
| 2010/0291061 A1 | 11/2010 | Jiang |
| 2011/0008417 A1 | 1/2011 | Peut et al. |
| 2011/0217307 A1 | 9/2011 | Hovenessian et al. |
| 2011/0277046 A1 | 11/2011 | Barton et al. |
| 2012/0082643 A1 | 4/2012 | Ruprecht et al. |
| 2012/0227120 A1 | 9/2012 | Hitchman et al. |
| 2012/0258126 A1 | 10/2012 | Scholler et al. |
| 2012/0308593 A1 | 12/2012 | Tartaglia et al. |
| 2013/0195904 A1 | 8/2013 | August et al. |
| 2013/0302364 A1 | 11/2013 | Mothe Pujadas et al. |
| 2015/0050310 A1 | 2/2015 | Brander et al. |
| 2015/0182618 A1 | 7/2015 | Stoloff et al. |
| 2018/0170971 A1 | 6/2018 | Brander et al. |
| 2019/0055289 A1 | 2/2019 | Brander et al. |
| 2021/0246172 A1 | 8/2021 | Brander et al. |
| 2022/0226459 A1 | 7/2022 | Brander et al. |

FOREIGN PATENT DOCUMENTS

| | | |
|---|---|---|
| EP | 1506223 B1 | 11/2005 |
| EP | 1773999 B1 | 9/2009 |
| EP | 2130921 A2 | 12/2009 |
| EP | 2292642 A1 | 3/2011 |
| EP | 2322626 A1 | 5/2011 |
| EP | 2358757 A1 | 8/2011 |
| EP | 2397489 A1 | 12/2011 |
| EP | 2402451 A2 | 1/2012 |
| EP | 1789438 B1 | 4/2015 |
| RU | 2 238 946 C2 | 10/2004 |
| WO | WO-9320212 A1 | 10/1993 |
| WO | WO 1996020013 | 7/1996 |
| WO | WO-9702355 A1 | 1/1997 |
| WO | WO 1997028816 | 8/1997 |
| WO | WO-2001049821 A2 | 7/2001 |
| WO | WO-0188141 A2 | 11/2001 |
| WO | WO-0232943 A2 | 4/2002 |
| WO | WO 2002042480 | 5/2002 |
| WO | WO-02068654 A2 | 9/2002 |
| WO | WO-03080112 A2 | 10/2003 |
| WO | WO-03097845 A1 | 11/2003 |
| WO | WO-2005028625 A2 | 3/2005 |
| WO | WO-2005030964 A1 | 4/2005 |
| WO | WO 2006010106 | 1/2006 |
| WO | WO-2006013106 A2 | 2/2006 |
| WO | WO-2006123256 A2 | 11/2006 |
| WO | WO-2007104932 A2 | 9/2007 |
| WO | WO-2008134068 A2 | 11/2008 |
| WO | WO-2008142479 A2 | 11/2008 |
| WO | WO-2009009743 A2 | 1/2009 |
| WO | WO-2010009346 A2 | 1/2010 |
| WO | WO 2010037402 | 4/2010 |
| WO | WO-2011042180 A1 | 4/2011 |
| WO | WO-2011047324 A1 | 4/2011 |
| WO | WO-2012062873 A2 | 5/2012 |
| WO | WO-2013110818 A2 | 8/2013 |
| WO | WO-2020234839 A1 | 11/2020 |

OTHER PUBLICATIONS

West, Jr., A. P., et al., Feb. 2014, Structural insights on the role of antibodies in HIV-1 vaccine and therapy, Cell 156:633-648.*
Adler, M., et al., "Range and Natural History of Infection," *Brit. Med. J.*, 294:1145-1147, BMA, United Kingdom (1987).
Altman, J., et al., "Formation of functional peptide complexes of class II major histocompatibility complex proteins from subunits produced in *Escherichia coli,"* *Proc. Natl. Acad. Sci. USA*, 90:10330-10334, U.S. National Academy of Sciences, United States (1993).
Altman, J., et al., "Phenotypic Analysis of Antigen-Specific T Lymphocytes," *Science*, 274:94-96, American Association for the Advancement of Science, United States (1996).
Altschul, S., et al., "Basic Local Alignment Search Tool," *J. Mol. Biol.*, 215:403-410, Academic Press Limited, United States (1990).
Altschul, S., et al., "Gapped BLAST and PSI-BLAST: a new generation of protein database search programs," *Nuc. Acids Res.*, 25(17):3389-3402, Oxford University Press, England (1997).
Andre, S., et al., "Increased Immune Response Elicited by DNA Vaccination with a Synthetic gp120 Sequence with Optimized Codon Usage," *J. Virol.*, 72(2):1497-1503, American Society for Microbiology, United States (1998).
Auer, H., "Determining the meaning of claim terms," *Nature Biotechnol.,*, 24:41-43, Nature Research, United Kingdom (2006).
Betts, M., et al., "Sensitive and viable identification of antigen-specific CD8+ T cells by a flow cytometric assay for degranulation," *J. Immunol. Methods*, 281:65-78, Elsevier, Netherlands (2003).
Brander, C., et al., "The challenges of host and viral diversity in HIV vaccine design," *Current Opinion Immunol.*, 18:430-437, Elsevier, Netherlands (2006).
Brockman, M., et al., "Escape and Compensation from Early HLA-B57 Mediated Cytotoxic T-Lymphocyte Pressure on Human Immunodeficiency Virus Type 1 Gag Alter Capsid Interactions with Cyclophilin A," *J. Virol.*, 81 (22):12608-12618, American Society for Microbiology, United States (2007).
Burke, S., et al., "The Inflation of Adjuvant on the Therapeutic Efficacy of a Recombinant Genital Herpes Vaccine," *J. Inf. Dis.*, 170:1110-1119, The University of Chicago, United States (1994).
Chattopadhyay, P., et al., "A live-cell assay to detect antigen-specific CD4+ T cells with diverse cytokine profiles," *Nat. Med.*, 11(10):1113-1117, Nature Research, United Kingdom (2005).
Claverie, J.M., et al., "T-immunogenic peptides are constituted of rare sequence patterns. Use in the identification of T epitopes in the human immunodeficiency virus gag protein," *Eur. J. Immunol.*, 18(10):1547-1553, VCH verlagsgesellschaft mbh, Germany (1988).
Davis, H., et al., "DNA-based immunization induces continuous secretion of hepatitis B surface antigen and high level of circulating antibody," *Hum. Mol. Gen.*, 2(11):1847-1851, Oxford University Press, England (1993).
Davis, H., et al., "Direct gene transfer in skeletal muscle: plasmid DNA-based immunization against the hepatitis B virus surface antigen," *Vaccine*, 12(16):1503-1509, Butterworth-Heinemann, United Kingdom (1994).
Extended European Search Report for EP12382031.8 dated Dec. 12, 2012, 4 pages.
Feng, L., et al., "High-Level Expression and Mutagenesis of Recombinant Human Phosphatidylcholine Transfer Protein Using a Synthetic Gene: Evidence for a C-Terminal Membrane Binding Domain," *Biochemistry*, 39(50):15399-15409, American Chemical Society, United States (2000).
Frahm, N., et al., "Consistent Cytotoxic-T-Lymphocyte targeting of Immunodominant Region in Human Immunodeficiency Virus across Multiple Ethnicities," *J. Virol.*, 78(5):2187-2200, American Society for Microbiology, United States (2004).
Frahm, N., et al., "Control of human immunodeficiency virus replication by cytotoxic T lymphocytes targeting subdominant epitopes," *Nat. Immunol.*, 7(2):173-178, Nature Publishing Group, United Kingdom (2006).
Frentsch, M., et al., "Direct access to CD4+ T cells specific for defined antigens according to CD154 expression," *Nat. Med.*, 11(10):1118-1124, Nature Research, United Kingdom (2005).
Friedrich, T., et al., "Subdominant CD8+ T-Cell Responses Are Involved in Durable Control of AIDS Virus Replication," *J. Virol.*,

(56) References Cited

OTHER PUBLICATIONS

81(7):3465-3476, American Society for Microbiology, United States (2007).

Hoffman, S., et al., "Protection against malaria by immunization with a *Plasmodium yoelii* circumsporozoite protein nucleic acid vaccine," *Vaccine*, 12(16):1529-1533, Butterworth-Heinemann, United Kingdom (1994).

Honeyborne, I., et al., "Control of Human Immunodeficiency Virus Type 1 Is Associated with HLA-B*13 and Targeting of Multiple Gag-Specific CD8+ T-Cell Epitopes," *J. Virol.*, 51:3667-3672, American Society for Microbiology, United States (2007).

Humphreys, D., et al., "High-Level Periplasmic Expression in *Escherichia coli* Using a Eukaryotic Signal Peptide: Importance of Codon Usage at the 5' End of the Coding Sequence," *Protein Expr. Purif.*, 20(2):252-264, Academic Press, United States (2000).

International Search Report for PCT/EP2013/051596 dated Sep. 20, 2013, 7 pages.

Johnson, V., et al., "2011 Update of the Drug Resistance Mutation in HIV-1," *ISA-USA Topics Antiviral Med.*, 19(4):156-164, International Antiviral Society, United States (2011).

Johnston, S., et al., "Gene Gun Transfection of Animal Cells and Genetic Immunization," in *Meth. Cell Biol.*, Chapter 17,, 43:353-364, Academic Press, United States (1994).

Kiepiela, P., et al., "Dominant influence of HLA-B in mediating the potential co-evolution of HIV and HLA," *Nature*, 432:769-775, Nature Publishing Group, United Kingdom (2004).

Kiepiela, P., et al., "CD8+ T-cell responses to difference HIV proteins have discordant associations with viral load," *Nat. Med.*, 13(1):46-53, Nature Publishing Group, United Kingdom (2007).

Leslie, A., et al., "HIV evolution: CTL escape mutation and reversion after transmission," *Nat. Med.*, 10:282-289 with Supplemental Information, Nature Publishing Group, United Kingdom (2004).

Mannering, S., et al., "A sensitive method for detecting proliferation of rare autoantigen-specific human T cells," *J. Immunol. Methods*, 283:173-183, Elsevier, Netherlands (2003).

Mayr, A., et al., "Abstammung, Eigenschaften und Verwendung des attenuierten Vaccinia-Stammes MVA," *Infection*, 3(1):6-14 (1975).

Mothe, B., et al., "Definition of the viral targets of protective HIV-1-specific T cell responses," *J. Trans. Med.*, 9(1):1-20, BioMed Central, United Kingdom (2011).

Mothe, B., et al., "A minimal T-cell immunogen designed to cover HIV-1 specificities associated with control is immunogenic in mice and breaks CTL immunodominance," *Retrovirology*, 9(2):P305, BioMed Central, United Kingdom (2012).

Narum, D., et al., "Codon Optimization of Gene Fragments Encoding Plasmodium falciparum Merzoite Proteins Enhances DNA Vaccine Protein Expression and Immunogenicity in Mice," *Infect. Immun.*, 9(12):7250-7253, American Society for Microbiology, United States (2001).

Ngumbela, K., et al., "Targeting if a CD8 T Cell Env Epitope Presented by HLA-B*5802 is Associated with Markers of HIV Disease Progression and Lack of Selection Pressure, " *AIDS Res. Hum. Retroviruses*, 24(1):72-82, Mary Ann Lievert, Inc. United States (2008).

Nickle, D., et al., "Consensus and Ancestral State HIV Vaccines," *Science*, 299:1515-1517, American Association for the Advancement of Science, United States (2003).

Novak, E., et al., MHC class II tetramers identify peptide-specific human CD4+ T cells proliferating in response to influenza A antigen, *J. Clin. Invest.*, 104:R63-R67, American Society for Clinical Investigation, United States (1999).

Outchkourov, N., et al., "Optimization of the expression of Equistatin in Pichia pastoris," *Protein Expr. Purif.*, 24(1):18-24, Elsevier, Netherlands (2002).

Robinson, H., et al., "Protection against a lethal influenza virus challenge by immunization with a haemagglutinin-expressing plasmid DNA," *Vaccine*, 11(9):957-960, Butterworth-Heinemann Ltd., United Kingdom (1993).

Rosati, M., et al., "DNA vaccination in rhesus macaques induces potent immune responses and decreases acute chronic viremia after SIVmac251 challenge," *Proc. Natl. Acad. Sci., USA*, 106:15831-15836, United States National Academy of Sciences, United States (2009).

Schneidewind, A., et al., "Escape from the Dominant HLA-B27-Restricted Cytotoxic T-Lymphocyte Response in Gag Is Associated with a Dramatic Reduction in Human Immunodeficiency Virus Type 1 Replication," *J. Virol.*, 81(22):12382-12393, American Society for Microbiology, United States (2007).

Schwartz, S., et al., "Mutational Inactivation of an Inhibitory Sequences in Human Immunodeficiency Virus Type 1 Results in Rev-Independent gag Expression," *J. Virol.*, 66(12), 7176-7182, American Society for Microbiology, United States (1992).

Shafer, R., Assay for antiretroviral resistance, HIV insite knowledge base chapter (http://hivinsite.ucsf.edu/InSite?page=kb-02-02-03, Jan. 2012).

Shafer, R., et al., "HIV-1 Drug Resistance Mutations: an Updated Framework for the Second Decade of HAARt," *AIDS Rev.*, 10(2):67-84, Permanyer Publications, Spain (2008).

Terpe, K., "Overview of tag protein fusions from molecular and biochemical fundamentals to commercial system," *Appl. Microbial. Biotechnol.*, 60:523-525, Springer-Verlag, Germany (2003).

Tigges, M., et al., "Human Herpes Simplex Virus (HSV)-Specific CD8= CTL Clones Recognize HSV-2-lnfected Fibroblasts after Treatment with IFN-$\gamma$ or When Virion Host Shutoff Functions Are Disabled," *J. Immunol.*, 156:3901-3910, American Association of Immunologists, United States (1996).

Watanabe, M., et al., "Liposome-Mediated DNA Transfer Into Chicken Primordial Germ Cells In Vitro," *Mol. Reprod. Dev.*, 38:268-274, Wiley-Liss, Inc., United States (1994).

Webster, R., et al., "Protection of ferrets against influenza challenge with a DNA vaccine to the haemagglutinin," *Vaccine*, 12:1495-1498, Butterworth-Heinemann Ltd., United Kingdom (1994).

Xiang, Z., et al., Vaccination with a Plasmid Vector Carrying the Rabies Virus Glycoprotein Gene Induces Protective Immunity Against Rabies Virus, *Virology*, 199:132-140, Academic Press, Inc., United States (1994).

Yerly, D., et al., "Increased Cytotoxic T-Lymphocyte Epitope Variant Cross-Recognition and Functional Avidity Are Associated with Hepatitis C Virus Clearance," *J. Virol.*, 82(6):3147-3153, American Society for Microbiology, United States (2008).

Zuniga, R., et al., "Relative Dominance of Gag p24-Specific Cytotoxic T Lymphocytes is Associated with Human Immunodeficiency Virus Control," *J. Virol.*, 80(6):3122-3125, American Society for Microbiology, United States (2006).

Arnold, P., et al., "The Majority of Immunogenic Epitopes Generate CD4+ T Cells That Are Dependent on MHC Class II-Bound Peptide-Flanking Residues," *The Journal of Immunology* 169: 739-749, The American Association of Immunologists, United States (2002).

Correia, B.E., et al., "Proof of principle for epitope-focused vaccine design," *Nature* 507(7491): 201-206, Nature Publishing Group, England (2014).

Desai, D., and Kulkarni-Kale, U., "T-Cell Epitope Prediction Methods: An Overview," in *Immunoinformatics, Methods in Molecular Biology*, vol. 1184, De, Rajat K., and Tomar, Namrata (Eds.), Springer Science+Business Media, United States (2014).

French, S., and Robson, B., "What is a Conservative Substitution," *Journal of Molecular Evolution* 19:171-175, Springer-Verlag, Germany (1983).

Huarte, E., "Enhancing Immunogenicity of a CTL Epitope from Carcinoembryonic Antigen by Selective Amino Acid Replacements," *Clinical Cancer Research* 8, 2336-2344, American Association for Cancer Research, United States (2002).

Masemola, A., "Novel and Promiscuous CTL Epitopes in Conserved Regions of Gag Targeted by Individuals with Early Subtype C Hiv Type 1 Infection from Southern Africa," Journal of Immunology, 173: 4607-4617 (2004).

Shang, X., et al., "Rational optimization of tumor epitopes using in silico analysis-assisted substitution of TCR contact residues," European Journal of Immunology 39: 2248-2258, WILEY-VCH Verlag GmbH & Co. KGaA, Germany (2009).

(56) References Cited

OTHER PUBLICATIONS

Salvat, R., et al., "Computationally driven deletion of broadly distributed T cell epitopes in a biotherapeutic candidate," Cellular and Molecular Life Sciences 77:4869-4880, Springer, Switzerland (2014).
Boggiano, C., et al., "Discovery and characterization of highly immunogenic and broadly recognized mimics of the HIV-1 Ctl epitope Gag77-85," European Journal of Immunology 35:1428-1437, WILEY-VCH Verlag GmbH & Co. KGaA, Germany (2005).
Ondondo, B., et al., "Novel Conserved-region T-cell Mosaic Vaccine With High Global HIV-1 Coverage is Recognized by Protective Responses in Untreated Infection," Molecular therapy: The American Society of Gene & Cell Therapy 24:832-842, United States (2016).
Ebner, C., et al., "Identification of Multiple T Cell Epitopes on Bet v 1, the Major Birch Pollen Allergen, Using Specific T Cell Clones and Overlapping Peptides," The Journal of Immunology 150:1047-1057, American Association of Immunologists, United States (1993).
Bazhan, S.I., et al., "Rational design based synthetic polyepitope DNA vaccine for eliciting HIV-specific CD8+ T cell responses," Molecular Immunology 47:1507-1515, Elsevier, Netherlands (2010).
Robbins, K.E., et al. "Molecular Analysis in Support of an Investigation of a Cluster of HIV-1-Infected Women.," Aids Res. Human Retro. 18(15): 1157-1161, Mary Ann Liebert, Inc., United States (2002).
Mcgettigan, J.P., et al. "Functional Human Immunodeficiency Virus Type 1 (HIV-1) Gag-Pol or HIV-1 Gag-Pol and Env Expressed from a Single Rhabdovirus-Based Vaccine Vector Genome," J. Virol., 77(20): 10889-10899, American Society for Microbiology, United States (2003).
Mamadou et al. NCBI GenBank Accession Nos. CAD48448 and CAD48441; 2005.
Brennan et al. NCBI GenBankAB061580.1,2006.
Kusk et al. NCBI GenBank Accession No. AAB24615; 1993.
Morellet et al. NCBI GenBank Accession No. 1U57_A; 2005.
Zhang et al. NCBI GenBank Accession No. AAB83205.1; 1997.
Masquelier et al. NCBI GenBank Accession No. CAB51523; 1999.
Ntemgwa et al. NCBI GenBank Accession No. ABU62725.1,2007.
Gatanaga et al. NCBI GenBank Accession No. BA017739.1; 2007.
John et al. NCBI GenBank Accession No. ADF87031,2010.
Powell et al. NCBI GenBank Accession No. ADF35429.1; 2009.
Saurya.S. NCBI GenBank Accession No. CAD23386; 2005.
Duque et al. NCBI GenBankAccession numberAAQ17444.1; 2003.
JK Wong, Ncb I GenBank Accession No. AAB08224.1; 1996.
Sette, A., et al. "The Development of Multi-epitope Vaccines: Epitope Identification, Vaccine Design and Clinical Evaluation," Biologicals, 29: 271-276, The International Association for Biologicals, United States (2001).
Brumme, Z.L. NCBI GenBank Accession No. ABY78164; 2010.
Frankel, A.D., "HIV-1: Fifteen Proteins and an RNA," Annual Rev. Biochem. 67:1-25, Annual Reviews, United States (1998).
Hancock, G., et al., "Identification of effective Subdominant Anti-Hiv-1 CD8+ T Cells within Entire Post-infection and Post-Vaccination Immune Responses," Public Library of Science Pathogens:1004658, Public Library of Science, United States (2015).
Autran, B., et al., "Greater viral rebound and reduced time to resume antiretroviral therapy after therapeutic immunization with the ALVAC-HIV vaccine (vCP1452)," AIDS, 22(11):1313-1322, Lippincott Williams & Wilkins, United States (2008).
Barouch, D.H., et al., "Protective Efficacy of Global HIB-1 Mosaic Vaccine Against Heterologous SHIV Challenges in Rhesus Monkeys," Cell, 155(3):531-539 with Supplemental Information, Elsevier, Inc., Netherlands (2013).
Buchbinder, S.P., et al., "Efficacy assessment of a cell-mediated immunity HIV-1 vaccine (the Step Study): a double-blind, randomized, placebo-controlled, test-of-concept trial," Lancet, 372(9653):1881-1893, Elsevier, Netherlands (2008).
Buzón, M., et al., "HIV-1 replication and immune dynamics are affected by raltegravir intensification of HAART-suppressed subjects," Nat Med., 16(4):460-465 with Supplemental Information, Springer Nature Limited, United Kingdom (2010).
Dinges, W.L., et al., "Virus-Specific CD8+ T-Cell Responses Better Define HIV Disease Progression that HLA Genotype," J Virol., 84(9):4461-4468, American Society for Microbiology, United States (2010).
El-Sadr, W.M., et al., CH4+ count-guided interruption of antiretroviral treatment, N Engl J Med., 355(22):2283-2296, Massachusetts Medical Society, United States (2006).
García, F., et al., "A Dendritic Cell-Based Vaccine Elicits T Cell Responses Associated with Control of HIV-1 Replication," Sci Transl Med., 5(166):166ra2, American Association forthe Advancement of Science, United States (2013).
Hammer, S.M., et al., "Efficacy Trial of a DNA/rAd5 HIV-1 Preventive Vaccine," N Engl J Med., 369(22):2083-2092, Massachusetts Medical Society, United States (2013).
Harrer, T., et al., "Safety and immunogenicity of an adjuvanted protein therapeutic HIV-1 vaccine in subjects with HIV-1 infection: a randomized placebo-controlled study," Vaccine, 32(22):2657-2665, Elsevier, Netherlands (2014).
Kilpeläinen, A., et al., "Recombinant BCG Expressing HTI Prime and Recombinant ChAdOx1 Boost Is Safe and Elicits HIV-1-Specific T-Cell Responses in BALB/c Mice," Vaccines, 7(3): 78, pp. 1-19, MDPI, Switzerland (Aug. 2019).
Kulkarni, V. R., et al., "HIV-1 p24$^{gag}$ Derived Conserved Element DNA Vaccine Increases the Breadth of Immune Response in Mice," PLoS One, 8(3):e60245, pp. 1-13, PLOS, United States (2013).
Kulkarni, V., et al., "Altered Response Hierarchy and Increased T-Cell Breadth Upon HIV-1 Conserved Element DNA Vaccination in Macaques," PLoS One, 9(1):e86254, pp. 1-13, PLOS, United States (2014).
Kunwar, P., et al., "Superior Control of HIV-1 Replication by CD8+ T Cells Targeting Conserved Epitopes: Implications for HIV Vaccine Design," PLoS One, 8(5):e64405, pp. 1-13, PLOS, United States (2013).
Létourneau, S., et al., "Design and Pre-Clinical Evaluation of a Universal HIV-1 Vaccine," PLoS One, 2(10):e984, pp. 1-11, PLOS, United States (2007).
Moltó, J., et al., "Influence of Prior Structured Treatment Interruptions on the Length of Time without Antiretroviral Treatment in Chronically HIV-Infected Subjects," AIDS Res Hum Retroviruses, 20(12):1283-1288, Mary Ann Liebert, Inc., United States (2004).
Mothe, B., et al., "A human immune data-informed vaccine concept elicits strong and broad T-cell specificities associated with HIV-1 control in mice and macaques," J Transl Med., 13(1):60, pp. 1-23, BioMed Central, United Kingdom (2015).
Mothe, B., et al., "Viral Control Induced by HIVCONSV Vaccines & Romidepsin in Early Treated Individuals," CROI, Feb. 13-16, 2017, Session O-11, Abstract No. 119LB, HIV Persistence and Reactivation, available at https://www.croiconference.org/abstract/viral-control-induced-hivconsv-vaccines-romidepsin-early-treated-individuals/ (last accessed on Apr. 9, 2021).
Niu, L., et al., "Preclinical evaluation of HIV-1 therapeutic ex vivo dendritic cell vaccines expressing consensus Gag antigens and conserved Gag epitopes," Vaccine, 29(11):2110-2119 with Supplemental Information, Elsevier, Netherlands (2011).
Pereyra, F., et al., "HIV Control Is Mediated in Part by CD8+ T-Cell Targeting of Specific Epitopes," J Virol., 88(22):12937-12948, American Society for Microbiology, United States (2014).
Ranasinghe, S.M., et al., "HIV-Specific CD4 T Cell Responses to Different Viral Proteins Have Discordant Associations with Viral Load and Clinical Outcome," J Virol., 86(1):277-83, American Society for Microbiology, United States (2012).
Ranasinghe, S., et al., "Association of HLA-DRB1-restricted CD4+ T cell responses with HIV immune control," Nat Med., 19(7):930-963 with Supplemental Information, Springer Nature Limited, United Kingdom (2013).
Rerks-Ngarm, S., et al., "Vaccination with ALVAC and AIDSVAX to Prevent HIV-1 Infection in Thailand," N Engl J Med., 361(23):2209-2220, Massachusetts Medical Society, United States (2009).
Rolland, M., et al., "HIV-1 group M Conserved Elements Vaccine," PLoS Pathogens, 3(11): e157, pp. 1551-1555, PLOS Pathogens, United States (2007).

(56) References Cited

OTHER PUBLICATIONS

Rolland, M., et al., "Genetic impact of vaccination on breakthrough HIV-1 sequences from the STEP trial," *Nat Med.*, 17(3):366-371 with Supplemental Information, Springer Nature Limited, United Kingdom (2011).

Schooley, R.T., et al., "AIDS Clinical Trials Group 5197: A Placebo-Controlled Trial of Immunization of HIV-1-Infected Persons with a Replication-Deficient Adenovirus Type 5 Vaccine Expressing the HIV-1 Core Protein," *J Infect Dis.*, 202(5):705-716, Oxford University Press, England (2010).

International Search Report and Written Opinion in International Application No. PCT/IB2020/060675, dated Mar. 3, 2021, 18 pages.

Anonymous, "Summary Notification Information Format for the Release of Genetically Modified Organisms Other Than Higher Plants in Accordance With Article 11 of Directive 2001/18/Ec," Aug. 17, 2018, 43 pages.

Kardani, K., et al., "Prime-boost vaccine strategy against viral infections: Mechanisms and benefits," *Vaccine*, 34:413-423, Elsevier, Netherlands (2016).

\* cited by examiner

SEQUENCE LISTING

```
<160> NUMBER OF SEQ ID NOS: 101

<210> SEQ ID NO 1
<211> LENGTH: 78
<212> TYPE: PRT
<213> ORGANISM: Artificial Sequence
<220> FEATURE:
<223> OTHER INFORMATION: OLP HIV clade B consensus sequence

<400> SEQUENCE: 1

Glu Lys Ile Arg Leu Arg Pro Gly Gly Lys Lys Tyr Lys Leu Lys
1               5                   10                  15

His Ile Val Trp Ala Ser Arg Glu Leu Glu Arg Phe Ala Val Asn Pro
            20                  25                  30

Gly Leu Leu Glu Thr Ser Glu Gly Cys Arg Gln Ile Leu Gly Gln Leu
        35                  40                  45

Gln Pro Ser Leu Gln Thr Gly Ser Glu Glu Leu Lys Ser Leu Tyr Asn
    50                  55                  60

Thr Val Ala Thr Leu Tyr Cys Val His Gln Lys Ile Glu Val
65                  70                  75

<210> SEQ ID NO 2
<211> LENGTH: 14
<212> TYPE: PRT
<213> ORGANISM: Artificial Sequence
<220> FEATURE:
<223> OTHER INFORMATION: OLP HIV clade B consensus sequence

<400> SEQUENCE: 2

Lys Ala Phe Ser Pro Glu Val Ile Pro Met Phe Ser Ala Leu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: OLP HIV clade B consensus sequence

<400> SEQUENCE: 3
```

```
Gly His Gln Ala Ala Met Gln Met Leu Lys Glu
1               5                   10

<210> SEQ ID NO 4
<211> LENGTH: 60
<212> TYPE: PRT
<213> ORGANISM: Artificial Sequence
<220> FEATURE:
<223> OTHER INFORMATION: OLP HIV clade B consensus sequence

<400> SEQUENCE: 4

Ile Ala Pro Gly Gln Met Arg Glu Pro Arg Gly Ser Asp Ile Ala Gly
1               5                   10                  15

Thr Thr Ser Thr Leu Gln Glu Gln Ile Gly Trp Met Thr Asn Asn Pro
            20                  25                  30

Pro Ile Pro Val Gly Glu Ile Tyr Lys Arg Trp Ile Ile Leu Gly Leu
        35                  40                  45

Asn Lys Ile Val Arg Met Tyr Ser Pro Thr Ser Ile
    50                  55                  60

<210> SEQ ID NO 5
<211> LENGTH: 14
<212> TYPE: PRT
<213> ORGANISM: Artificial Sequence
<220> FEATURE:
<223> OTHER INFORMATION: OLP HIV clade B consensus sequence

<400> SEQUENCE: 5

Tyr Val Asp Arg Phe Tyr Lys Thr Leu Arg Ala Glu Gln Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: OLP HIV clade B consensus sequence

<400> SEQUENCE: 6

Ala Cys Gln Gly Val Gly Gly Pro Gly His Lys Ala Arg Val Leu
1               5                   10                  15

<210> SEQ ID NO 7
<211> LENGTH: 27
<212> TYPE: PRT
<213> ORGANISM: Artificial Sequence
<220> FEATURE:
<223> OTHER INFORMATION: OLP HIV clade B consensus sequence

<400> SEQUENCE: 7

Cys Thr Glu Arg Gln Ala Asn Phe Leu Gly Lys Ile Trp Pro Ser His
1               5                   10                  15

Lys Gly Arg Pro Gly Asn Phe Leu Gln Ser Arg
            20                  25

<210> SEQ ID NO 8
<211> LENGTH: 55
<212> TYPE: PRT
<213> ORGANISM: Artificial Sequence
<220> FEATURE:
<223> OTHER INFORMATION: OLP HIV clade B consensus sequence

<400> SEQUENCE: 8

Lys Met Ile Gly Gly Ile Gly Gly Phe Ile Lys Val Arg Gln Tyr Asp
```

```
1               5                   10                  15
Gln Ile Leu Ile Glu Ile Cys Gly His Lys Ala Ile Gly Thr Val Leu
        20                  25                  30

Val Gly Pro Thr Pro Val Asn Ile Ile Gly Arg Asn Leu Leu Thr Gln
            35                  40                  45

Ile Gly Cys Thr Leu Asn Phe
        50                  55
```

<210> SEQ ID NO 9
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 9

```
Leu Val Glu Ile Cys Thr Glu Leu Glu Lys Glu Gly Lys Ile Ser Lys
1               5                   10                  15

Ile
```

<210> SEQ ID NO 10
<211> LENGTH: 55
<212> TYPE: PRT
<213> ORGANISM: Artificial Sequence
<220> FEATURE:
<223> OTHER INFORMATION: OLP HIV clade B consensus sequence

<400> SEQUENCE: 10

```
Leu Arg Trp Gly Phe Thr Thr Pro Asp Lys Lys His Gln Lys Glu Pro
1               5                   10                  15

Pro Phe Leu Trp Met Gly Tyr Glu Leu His Pro Asp Lys Trp Thr Val
            20                  25                  30

Gln Pro Ile Val Leu Pro Glu Lys Asp Ser Trp Thr Val Asn Asp Ile
        35                  40                  45

Gln Lys Leu Val Gly Lys Leu
        50                  55
```

<210> SEQ ID NO 11
<211> LENGTH: 34
<212> TYPE: PRT
<213> ORGANISM: Artificial Sequence
<220> FEATURE:
<223> OTHER INFORMATION: OLP HIV clade B consensus sequence

<400> SEQUENCE: 11

```
Ile Leu Lys Glu Pro Val His Gly Val Tyr Tyr Asp Pro Ser Lys Asp
1               5                   10                  15

Leu Ile Ala Glu Ile Gln Lys Gln Gly Gln Gly Gln Trp Thr Tyr Gln
            20                  25                  30

Ile Tyr
```

<210> SEQ ID NO 12
<211> LENGTH: 34
<212> TYPE: PRT
<213> ORGANISM: Artificial sequence
<220> FEATURE:
<223> OTHER INFORMATION: OLP HIV clade B consensus sequence

<400> SEQUENCE: 12

```
Thr Lys Glu Leu Gln Lys Gln Ile Thr Lys Ile Gln Asn Phe Arg Val
1               5                   10                  15
```

```
Tyr Tyr Arg Asp Ser Arg Asp Pro Leu Trp Lys Gly Pro Ala Lys Leu
            20                  25                  30

Leu Trp

<210> SEQ ID NO 13
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 13

Lys Ile Ile Arg Asp Tyr Gly Lys Gln Met Ala Gly Asp Asp Cys Val
1               5                   10                  15

Ala

<210> SEQ ID NO 14
<211> LENGTH: 26
<212> TYPE: PRT
<213> ORGANISM: Artificial Sequence
<220> FEATURE:
<223> OTHER INFORMATION: OLP HIV clade B consensus sequence

<400> SEQUENCE: 14

Val Lys His His Met Tyr Ile Ser Lys Lys Ala Lys Gly Trp Phe Tyr
1               5                   10                  15

Arg His His Tyr Glu Ser Thr His Pro Arg
            20                  25

<210> SEQ ID NO 15
<211> LENGTH: 19
<212> TYPE: PRT
<213> ORGANISM: Artificial Sequence
<220> FEATURE:
<223> OTHER INFORMATION: OLP HIV clade B consensus sequence

<400> SEQUENCE: 15

Val Thr Lys Leu Thr Glu Asp Arg Trp Asn Lys Pro Gln Lys Thr Lys
1               5                   10                  15

Gly His Arg

<210> SEQ ID NO 16
<211> LENGTH: 13
<212> TYPE: PRT
<213> ORGANISM: Artificial Sequence
<220> FEATURE:
<223> OTHER INFORMATION: OLP HIV clade B consensus sequence

<400> SEQUENCE: 16

Ala Trp Leu Glu Ala Gln Glu Glu Glu Glu Val Gly Phe
1               5                   10

<210> SEQ ID NO 17
<211> LENGTH: 23
<212> TYPE: PRT
<213> ORGANISM: Artificial Sequence
<220> FEATURE:
<223> OTHER INFORMATION: OLP HIV clade B consensus sequence

<400> SEQUENCE: 17

Glu Lys Ile Arg Leu Arg Pro Gly Gly Lys Lys Tyr Lys Leu Lys
1               5                   10                  15

His Ile Val Trp Ala Ser Arg
            20
```

<210> SEQ ID NO 18
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 18

Lys Leu Lys His Ile Val Trp Ala Ser Arg Glu Leu Glu Arg Phe Ala
1               5                   10                  15

Val Asn Pro Gly Leu Leu
            20

<210> SEQ ID NO 19
<211> LENGTH: 23
<212> TYPE: PRT
<213> ORGANISM: Artificial Sequence
<220> FEATURE:
<223> OTHER INFORMATION: OLP HIV clade B consensus sequence

<400> SEQUENCE: 19

Glu Arg Phe Ala Val Asn Pro Gly Leu Leu Glu Thr Ser Glu Gly Cys
1               5                   10                  15

Arg Gln Ile Leu Gly Gln Leu
            20

<210> SEQ ID NO 20
<211> LENGTH: 24
<212> TYPE: PRT
<213> ORGANISM: Artificial Sequence
<220> FEATURE:
<223> OTHER INFORMATION: OLP HIV clade B consensus sequence

<400> SEQUENCE: 20

Glu Gly Cys Arg Gln Ile Leu Gly Gln Leu Gln Pro Ser Leu Gln Thr
1               5                   10                  15

Gly Ser Glu Glu Leu Lys Ser Leu
            20

<210> SEQ ID NO 21
<211> LENGTH: 26
<212> TYPE: PRT
<213> ORGANISM: Artificial Sequence
<220> FEATURE:
<223> OTHER INFORMATION: OLP HIV clade B consensus sequence

<400> SEQUENCE: 21

Gln Thr Gly Ser Glu Glu Leu Lys Ser Leu Tyr Asn Thr Val Ala Thr
1               5                   10                  15

Leu Tyr Cys Val His Gln Arg Ile Glu Val
            20                  25

<210> SEQ ID NO 22
<211> LENGTH: 14
<212> TYPE: PRT
<213> ORGANISM: Artificial Sequence
<220> FEATURE:
<223> OTHER INFORMATION: OLP HIV clade B consensus sequence

<400> SEQUENCE: 22

Lys Ala Phe Ser Pro Glu Val Ile Pro Met Phe Ser Ala Leu
1               5                   10

-continued

```
<210> SEQ ID NO 23
<211> LENGTH: 11
<212> TYPE: PRT
<213> ORGANISM: Artificial Sequence
<220> FEATURE:
<223> OTHER INFORMATION: OLP HIV clade B consensus sequence

<400> SEQUENCE: 23

Gly His Gln Ala Ala Met Gln Met Leu Lys Glu
1               5                   10

<210> SEQ ID NO 24
<211> LENGTH: 21
<212> TYPE: PRT
<213> ORGANISM: Artificial Sequence
<220> FEATURE:
<223> OTHER INFORMATION: OLP HIV clade B consensus sequence

<400> SEQUENCE: 24

Ile Ala Pro Gly Gln Met Arg Glu Pro Arg Gly Ser Asp Ile Ala Gly
1               5                   10                  15

Thr Thr Ser Thr Leu
            20

<210> SEQ ID NO 25
<211> LENGTH: 23
<212> TYPE: PRT
<213> ORGANISM: Artificial Sequence
<220> FEATURE:
<223> OTHER INFORMATION: OLP HIV clade B consensus sequence

<400> SEQUENCE: 25

Ser Asp Ile Ala Gly Thr Thr Ser Thr Leu Gln Glu Gln Ile Gly Trp
1               5                   10                  15

Met Thr Asn Asn Pro Pro Ile
            20

<210> SEQ ID NO 26
<211> LENGTH: 24
<212> TYPE: PRT
<213> ORGANISM: Artificial Sequence
<220> FEATURE:
<223> OTHER INFORMATION: OLP HIV clade B consensus sequence

<400> SEQUENCE: 26

Ile Gly Trp Met Thr Asn Asn Pro Pro Ile Pro Val Gly Glu Ile Tyr
1               5                   10                  15

Lys Arg Trp Ile Ile Leu Gly Leu
            20

<210> SEQ ID NO 27
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 27

Ile Tyr Lys Arg Trp Ile Ile Leu Gly Leu Asn Lys Ile Val Arg Met
1               5                   10                  15

Tyr Ser Pro Thr Ser Ile
            20

<210> SEQ ID NO 28
<211> LENGTH: 14
```

```
<212> TYPE: PRT
<213> ORGANISM: Artificial Sequence
<220> FEATURE:
<223> OTHER INFORMATION: OLP HIV clade B consensus sequence

<400> SEQUENCE: 28

Tyr Val Asp Arg Phe Tyr Lys Thr Leu Arg Ala Glu Gln Ala
1               5                   10

<210> SEQ ID NO 29
<211> LENGTH: 15
<212> TYPE: PRT
<213> ORGANISM: Artificial Sequence
<220> FEATURE:
<223> OTHER INFORMATION: OLP HIV clade B consensus sequence

<400> SEQUENCE: 29

Ala Cys Gln Gly Val Gly Gly Pro Gly His Lys Ala Arg Val Leu
1               5                   10                  15

<210> SEQ ID NO 30
<211> LENGTH: 27
<212> TYPE: PRT
<213> ORGANISM: Artificial Sequence
<220> FEATURE:
<223> OTHER INFORMATION: OLP HIV clade B consensus sequence

<400> SEQUENCE: 30

Cys Thr Glu Arg Gln Ala Asn Phe Leu Gly Lys Ile Trp Pro Ser His
1               5                   10                  15

Lys Gly Arg Pro Gly Asn Phe Leu Gln Ser Arg
            20                  25

<210> SEQ ID NO 31
<211> LENGTH: 26
<212> TYPE: PRT
<213> ORGANISM: Artificial Sequence
<220> FEATURE:
<223> OTHER INFORMATION: OLP HIV clade B consensus sequence

<400> SEQUENCE: 31

Lys Met Ile Gly Gly Ile Gly Gly Phe Ile Lys Val Arg Gln Tyr Asp
1               5                   10                  15

Gln Ile Leu Ile Glu Ile Cys Gly His Lys
            20                  25

<210> SEQ ID NO 32
<211> LENGTH: 24
<212> TYPE: PRT
<213> ORGANISM: Artificial Sequence
<220> FEATURE:
<223> OTHER INFORMATION: OLP HIV clade B consensus sequence

<400> SEQUENCE: 32

Gln Ile Leu Ile Glu Ile Cys Gly His Lys Ala Ile Gly Thr Val Leu
1               5                   10                  15

Val Gly Pro Thr Pro Val Asn Ile
            20

<210> SEQ ID NO 33
<211> LENGTH: 25
<212> TYPE: PRT
<213> ORGANISM: Artificial Sequence
<220> FEATURE:
<223> OTHER INFORMATION: OLP HIV clade B consensus sequence
```

-continued

```
<400> SEQUENCE: 33

Val Leu Val Gly Pro Thr Pro Val Asn Ile Ile Gly Arg Asn Leu Leu
1               5                   10                  15

Thr Gln Ile Gly Cys Thr Leu Asn Phe
            20                  25

<210> SEQ ID NO 34
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 34

Leu Val Glu Ile Cys Thr Glu Met Glu Lys Glu Gly Lys Ile Ser Lys
1               5                   10                  15

Ile

<210> SEQ ID NO 35
<211> LENGTH: 25
<212> TYPE: PRT
<213> ORGANISM: Artificial Sequence
<220> FEATURE:
<223> OTHER INFORMATION: OLP HIV clade B consensus sequence

<400> SEQUENCE: 35

Leu Arg Trp Gly Phe Thr Thr Pro Asp Lys Lys His Gln Lys Glu Pro
1               5                   10                  15

Pro Phe Leu Trp Met Gly Tyr Glu Leu
            20                  25

<210> SEQ ID NO 36
<211> LENGTH: 25
<212> TYPE: PRT
<213> ORGANISM: Artificial Sequence
<220> FEATURE:
<223> OTHER INFORMATION: OLP HIV clade B consensus sequence

<400> SEQUENCE: 36

Pro Pro Phe Leu Trp Met Gly Tyr Glu Leu His Pro Asp Lys Trp Thr
1               5                   10                  15

Val Gln Pro Ile Val Leu Pro Glu Lys
            20                  25

<210> SEQ ID NO 37
<211> LENGTH: 25
<212> TYPE: PRT
<213> ORGANISM: Artificial Sequence
<220> FEATURE:
<223> OTHER INFORMATION: OLP HIV clade B consensus sequence

<400> SEQUENCE: 37

Thr Val Gln Pro Ile Val Leu Pro Glu Lys Asp Ser Trp Thr Val Asn
1               5                   10                  15

Asp Ile Gln Lys Leu Val Gly Lys Leu
            20                  25

<210> SEQ ID NO 38
<211> LENGTH: 23
<212> TYPE: PRT
<213> ORGANISM: Artificial Sequence
<220> FEATURE:
<223> OTHER INFORMATION: OLP HIV clade B consensus sequence
```

-continued

```
<400> SEQUENCE: 38

Ile Leu Lys Glu Pro Val His Gly Val Tyr Tyr Asp Pro Ser Lys Asp
1               5                   10                  15

Leu Ile Ala Glu Ile Gln Lys
            20

<210> SEQ ID NO 39
<211> LENGTH: 21
<212> TYPE: PRT
<213> ORGANISM: Artificial Sequence
<220> FEATURE:
<223> OTHER INFORMATION: OLP HIV clade B consensus sequence

<400> SEQUENCE: 39

Ser Lys Asp Leu Ile Ala Glu Ile Gln Lys Gln Gly Gln Gly Gln Trp
1               5                   10                  15

Thr Tyr Gln Ile Tyr
            20

<210> SEQ ID NO 40
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 40

Thr Lys Glu Leu Gln Lys Gln Ile Thr Lys Ile Gln Asn Phe Arg Val
1               5                   10                  15

Tyr Tyr Arg Asp Ser Arg
            20

<210> SEQ ID NO 41
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 41

Asn Phe Arg Val Tyr Tyr Arg Asp Ser Arg Asp Pro Leu Trp Lys Gly
1               5                   10                  15

Pro Ala Lys Leu Leu Trp
            20

<210> SEQ ID NO 42
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 42

Lys Ile Ile Arg Asp Tyr Gly Lys Gln Met Ala Gly Asp Asp Cys Val
1               5                   10                  15

Ala

<210> SEQ ID NO 43
<211> LENGTH: 26
<212> TYPE: PRT
<213> ORGANISM: Artificial Sequence
<220> FEATURE:
<223> OTHER INFORMATION: OLP HIV clade B consensus sequence
```

```
<400> SEQUENCE: 43

Val Lys His His Met Tyr Ile Ser Lys Lys Ala Lys Gly Trp Phe Tyr
1               5                   10                  15

Arg His His Tyr Glu Ser Thr His Pro Arg
            20                  25

<210> SEQ ID NO 44
<211> LENGTH: 19
<212> TYPE: PRT
<213> ORGANISM: Artificial Sequence
<220> FEATURE:
<223> OTHER INFORMATION: OLP HIV clade B consensus sequence

<400> SEQUENCE: 44

Val Thr Lys Leu Thr Glu Asp Arg Trp Asn Lys Pro Gln Lys Thr Lys
1               5                   10                  15

Gly His Arg

<210> SEQ ID NO 45
<211> LENGTH: 13
<212> TYPE: PRT
<213> ORGANISM: Artificial Sequence
<220> FEATURE:
<223> OTHER INFORMATION: OLP HIV clade B consensus sequence

<400> SEQUENCE: 45

Ala Trp Leu Glu Ala Gln Glu Glu Glu Glu Val Gly Phe
1               5                   10

<210> SEQ ID NO 46
<211> LENGTH: 17
<212> TYPE: PRT
<213> ORGANISM: Homo sapiens

<400> SEQUENCE: 46

Met Trp Leu Gln Ser Leu Leu Leu Leu Gly Thr Val Ala Cys Ser Ile
1               5                   10                  15

Ser

<210> SEQ ID NO 47
<211> LENGTH: 18
<212> TYPE: PRT
<213> ORGANISM: Artificial Sequence
<220> FEATURE:
<223> OTHER INFORMATION: human GM-CSF signal peptide + V

<400> SEQUENCE: 47

Met Trp Leu Gln Ser Leu Leu Leu Leu Gly Thr Val Ala Cys Ser Ile
1               5                   10                  15

Ser Val

<210> SEQ ID NO 48
<211> LENGTH: 9
<212> TYPE: PRT
<213> ORGANISM: Artificial Sequence
<220> FEATURE:
<223> OTHER INFORMATION: Flag-tag

<400> SEQUENCE: 48

Asp Tyr Lys Asp Asp Asp Asp Lys Leu
1               5

<210> SEQ ID NO 49
```

<211> LENGTH: 556
<212> TYPE: PRT
<213> ORGANISM: Artificial Sequence
<220> FEATURE:
<223> OTHER INFORMATION: HIV immunogen comprising OLPs

<400> SEQUENCE: 49

Met Trp Leu Gln Ser Leu Leu Leu Gly Thr Val Ala Cys Ser Ile
1               5                   10                  15

Ser Val Glu Lys Ile Arg Leu Arg Pro Gly Gly Lys Lys Tyr Lys
            20                  25                  30

Leu Lys His Ile Val Trp Ala Ser Arg Glu Leu Glu Arg Phe Ala Val
                35                  40                  45

Asn Pro Gly Leu Leu Glu Thr Ser Glu Gly Cys Arg Gln Ile Leu Gly
        50                  55                  60

Gln Leu Gln Pro Ser Leu Gln Thr Gly Ser Glu Leu Lys Ser Leu
65                  70                  75                  80

Tyr Asn Thr Val Ala Thr Leu Tyr Cys Val His Gln Lys Ile Glu Val
                85                  90                  95

Ala Ala Ala Lys Ala Phe Ser Pro Glu Val Ile Pro Met Phe Ser Ala
            100                 105                 110

Leu Ala Ala Gly His Gln Ala Ala Met Gln Met Leu Lys Glu Ala
            115                 120                 125

Ala Ala Ile Ala Pro Gly Gln Met Arg Glu Pro Arg Gly Ser Asp Ile
        130                 135                 140

Ala Gly Thr Thr Ser Thr Leu Gln Glu Gln Ile Gly Trp Met Thr Asn
145                 150                 155                 160

Asn Pro Pro Ile Pro Val Gly Glu Ile Tyr Lys Arg Trp Ile Ile Leu
                165                 170                 175

Gly Leu Asn Lys Ile Val Arg Met Tyr Ser Pro Thr Ser Ile Ala Ala
            180                 185                 190

Ala Tyr Val Asp Arg Phe Tyr Lys Thr Leu Arg Ala Glu Gln Ala Ala
        195                 200                 205

Ala Cys Gln Gly Val Gly Gly Pro Gly His Lys Ala Arg Val Leu Ala
210                 215                 220

Ala Ala Cys Thr Glu Arg Gln Ala Asn Phe Leu Gly Lys Ile Trp Pro
225                 230                 235                 240

Ser His Lys Gly Arg Pro Gly Asn Phe Leu Gln Ser Arg Ala Ala Ala
                245                 250                 255

Lys Met Ile Gly Gly Ile Gly Gly Phe Ile Lys Val Arg Gln Tyr Asp
            260                 265                 270

Gln Ile Leu Ile Glu Ile Cys Gly His Lys Ala Ile Gly Thr Val Leu
        275                 280                 285

Val Gly Pro Thr Pro Val Asn Ile Ile Gly Arg Asn Leu Leu Thr Gln
290                 295                 300

Ile Gly Cys Thr Leu Asn Phe Ala Ala Leu Val Glu Ile Cys Thr Glu
305                 310                 315                 320

Met Glu Lys Glu Gly Lys Ile Ser Lys Ile Ala Ala Ala Leu Arg Trp
                325                 330                 335

Gly Phe Thr Thr Pro Asp Lys Lys His Gln Lys Glu Pro Pro Phe Leu
            340                 345                 350

Trp Met Gly Tyr Glu Leu His Pro Asp Lys Trp Thr Val Gln Pro Ile
        355                 360                 365

Val Leu Pro Glu Lys Asp Ser Trp Thr Val Asn Asp Ile Gln Lys Leu
370                 375                 380

```
Val Gly Lys Leu Ala Ala Ile Leu Lys Glu Pro Val His Gly Val
385                 390                 395                 400

Tyr Tyr Asp Pro Ser Lys Asp Leu Ile Ala Glu Ile Gln Lys Gln Gly
            405                 410                 415

Gln Gly Gln Trp Thr Tyr Gln Ile Tyr Ala Ala Ala Thr Lys Glu Leu
        420                 425                 430

Gln Lys Gln Ile Thr Lys Ile Gln Asn Phe Arg Val Tyr Tyr Arg Asp
        435                 440                 445

Ser Arg Asp Pro Leu Trp Lys Gly Pro Ala Lys Leu Leu Trp Ala Ala
    450                 455                 460

Ala Lys Ile Ile Arg Asp Tyr Gly Lys Gln Met Ala Gly Asp Asp Cys
465                 470                 475                 480

Val Ala Ala Val Lys His His Met Tyr Ile Ser Lys Lys Ala Lys
                485                 490                 495

Gly Trp Phe Tyr Arg His His Tyr Glu Ser Thr His Pro Arg Ala Ala
            500                 505                 510

Ala Val Thr Lys Leu Thr Glu Asp Arg Trp Asn Lys Pro Gln Lys Thr
        515                 520                 525

Lys Gly His Arg Ala Ala Ala Trp Leu Glu Ala Gln Glu Glu Glu
    530                 535                 540

Val Gly Phe Asp Tyr Lys Asp Asp Asp Lys Leu
545                 550                 555

<210> SEQ ID NO 50
<211> LENGTH: 1674
<212> TYPE: DNA
<213> ORGANISM: Artificial Sequence
<220> FEATURE:
<223> OTHER INFORMATION: polynucleotide encoding immunogen comprising
      HIV OLPs

<400> SEQUENCE: 50
atgtggctcc agagcctgct actcctgggg acgtggcct gcagcatctc ggtcgagaag     60
atccggctgc ggccaggcgg aaagaagaag tacaagctga gcacatcgt ctgggcctcg    120 agggagctgg agcggttcgc ggtgaacccg ggacttctgg agacgtcgga ggggtgcagg    180
cagatcctcg gccagctgca gccctctctg caaacggggt ctgaggagct gaagagcctg    240
tacaacacgg tggcgaccct ctactgcgtc accagaaga tcgaggtggc agcggccaag    300
gcgttctcgc cggaggtcat ccccatgttc tcggcgctgg cagctgccgg acaccaggcc    360
gcgatgcaga tgctgaagga ggccgctgcg atcgcaccgg ccagatgag ggagccacgc    420 ggttccgaca tcgcgggaac cacctcgacg ctccaggagc agatcggatg gatgacgaac    480
aacccgccaa tccggtcgg ggagatctac aagcggtgga tcatcctcgg ctgaacaag    540 atcgtccgga tgtacagccc gacgtcgatc gctgcggcat acgttgaccg gttctacaag    600
accctgaggg ccgagcaggc agcggcctgc caggggggtcg gtggaccagg cacaaggcc    660 cgagtgctcg cggccgcatg cacggagcgg caggcgaact tcctgggaa gatctggccg    720 tcgcacaagg gccgaccggg aaacttcctc cagtctccgcg cagcggctaa gatgatcgga    780
ggcatcggag gcttcatcaa gtccgtcag tacgaccaga tcctcatcga gatctgcggg    840
cacaaggcga tcggaaccgt gctcgtcggc ccaacgcccg tgaacatcat cggccgcaac    900
ctgttaacgc agatcggctg cacctcaac ttcgccgcac tagtgagat ctgcacggag    960 atggagaagg agggcaagat atcgaagatc gcggcagctc tgaggtgggg cttcaccacg   1020
```

```
ccggacaaga agcaccagaa ggagccgcca ttcctgtgga tgggatacga gctgcacccg    1080
gacaagtgga ccgtgcagcc catcgtcctg ccggagaagg actcgtggac ggtgaacgac    1140
atccagaagc tcgtggggaa gctggcggca gccatcctca aggagcccgt ccacggggtg    1200
tactacgacc cctctaagga cctgatcgcg gagatccaga gcaggggca gggtcagtgg     1260 acctaccaga tctacgcagc agcaaccaag gagctgcaga agcagatcac gaagatccag    1320
aacttccgcg tatactaccg cgactcgcgg gaccccctgt ggaagggccc tgcgaagctt    1380
ctctgggcag ccgcgaagat catccgggac tacggcaagc agatggcggg cgacgactgc    1440
gtggccgcag cggtgaagca ccatatgtac atctcgaaga aggcgaaggg ctggttctac    1500
agacaccact acgagtccac ccaccccagg gcagctgcgg tgacgaagct gacggaggac    1560
cggtggaaca agccccagaa gacgaagggt caccgggcgg ctgcatggct ggaggctcag    1620
gaggaggagg aggtgggctt cgattacaag gacgatgacg acaagctgtg ataa          1674

<210> SEQ ID NO 51
<211> LENGTH: 60
<212> TYPE: DNA
<213> ORGANISM: Artificial Sequence
<220> FEATURE:
<223> OTHER INFORMATION: 198HPlus primer

<400> SEQUENCE: 51
gtcaccgggc ggctgcatgg ctggaggctc aggaggagga ggaggtgggc ttctgataag    60

<210> SEQ ID NO 52
<211> LENGTH: 59
<212> TYPE: DNA
<213> ORGANISM: Artificial Sequence
<220> FEATURE:
<223> OTHER INFORMATION: 298HMinus primer

<400> SEQUENCE: 52
aattcttatc agaagcccac ctcctcctcc tcctgagcct ccagccatgc agccgcccg     59

<210> SEQ ID NO 53
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 53

Glu Lys Ile Arg Leu Arg Pro Gly Gly Lys Lys Tyr Lys Leu Lys
1               5                   10                  15

His Ile

<210> SEQ ID NO 54
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 54

Ala Ser Arg Glu Leu Glu Arg Phe Ala Val Asn Pro Gly Leu Leu
1               5                   10                  15

<210> SEQ ID NO 55
<211> LENGTH: 17
<212> TYPE: PRT
<213> ORGANISM: Artificial Sequence
```

-continued

```
<220> FEATURE:
<223> OTHER INFORMATION: OLP clade B consensus sequence

<400> SEQUENCE: 55

Glu Arg Phe Ala Val Asn Pro Gly Leu Leu Glu Thr Ser Glu Gly Cys
1               5                   10                  15

Arg

<210> SEQ ID NO 56
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 56

Gln Leu Gln Pro Ser Leu Gln Thr Gly Ser Glu Glu Leu Arg Ser Leu
1               5                   10                  15

Tyr

<210> SEQ ID NO 57
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 57

Ser Leu Tyr Asn Thr Val Ala Thr Leu Tyr Cys Val His Gln Arg Ile
1               5                   10                  15

Glu Val

<210> SEQ ID NO 58
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 58

Ala Phe Ser Pro Glu Val Ile Pro Met Phe Ser Ala Leu Ser Glu Gly
1               5                   10                  15

Ala

<210> SEQ ID NO 59
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 59

Ile Ala Pro Gly Gln Met Arg Glu Pro Arg Gly Ser Asp Ile Ala
1               5                   10                  15

<210> SEQ ID NO 60
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 60

Ser Thr Leu Gln Glu Gln Ile Gly Trp Met Thr Asn Asn Pro Pro Ile
```

-continued

```
1               5                   10                  15

Pro Val

<210> SEQ ID NO 61
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 61

Ala Cys Gln Gly Val Gly Gly Pro Gly His Lys Ala Arg Val Leu Ala
1               5                   10                  15

Glu Ala

<210> SEQ ID NO 62
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 62

Gly Lys Ile Trp Pro Ser His Lys Gly Arg Pro Gly Asn Phe Leu Gln
1               5                   10                  15

Ser Arg

<210> SEQ ID NO 63
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 63

Trp Leu Glu Ala Gln Glu Glu Glu Val Gly Phe Pro Val Arg Pro
1               5                   10                  15

Gln Val

<210> SEQ ID NO 64
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 64

Glu Val Gly Phe Pro Val Arg Pro Gln Val Pro Leu Arg Pro Met Thr
1               5                   10                  15

Tyr Lys

<210> SEQ ID NO 65
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 65

Asn Tyr Thr Pro Gly Pro Gly Ile Arg Tyr Pro Leu Thr Phe Gly Trp
1               5                   10                  15

Cys Phe
```

<210> SEQ ID NO 66
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 66

Arg Tyr Pro Leu Thr Phe Gly Trp Cys Phe Lys Leu Val Pro Val
1               5                   10                  15

<210> SEQ ID NO 67
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 67

Ser Leu His Gly Met Asp Asp Pro Glu Lys Glu Val Leu Val Trp Lys
1               5                   10                  15

Phe

<210> SEQ ID NO 68
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 68

Lys Met Ile Gly Gly Ile Gly Gly Phe Ile Lys Val Arg Gln Tyr Asp
1               5                   10                  15

Gln Ile

<210> SEQ ID NO 69
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 69

Phe Ile Lys Val Arg Gln Tyr Asp Gln Ile Leu Ile Glu Ile Cys Gly
1               5                   10                  15

His Lys

<210> SEQ ID NO 70
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 70

Gln Ile Leu Ile Glu Ile Cys Gly His Lys Ala Ile Gly Thr Val Leu
1               5                   10                  15

Val

<210> SEQ ID NO 71
<211> LENGTH: 18
<212> TYPE: PRT
<213> ORGANISM: Artificial Sequence
<220> FEATURE:

-continued

<223> OTHER INFORMATION: OLP clade B consensus sequence

<400> SEQUENCE: 71

Leu Val Gly Pro Thr Pro Val Asn Ile Ile Gly Arg Asn Leu Leu Thr
1               5                   10                  15

Gln Ile

<210> SEQ ID NO 72
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 72

Leu Val Glu Ile Cys Thr Glu Met Glu Lys Glu Gly Lys Ile Ser Lys
1               5                   10                  15

Ile

<210> SEQ ID NO 73
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 73

Leu Asp Val Gly Asp Ala Tyr Phe Ser Val Pro Leu Asp Lys Asp Phe
1               5                   10                  15

Arg Lys

<210> SEQ ID NO 74
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 74

Leu Arg Trp Gly Phe Thr Thr Pro Asp Lys Lys His Gln Lys Glu Pro
1               5                   10                  15

Pro Phe

<210> SEQ ID NO 75
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 75

Asp Lys Lys His Gln Lys Glu Pro Pro Phe Leu Trp Met Gly Tyr Glu
1               5                   10                  15

Leu His

<210> SEQ ID NO 76
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 76

```
Glu Ile Gln Lys Gln Gly Gln Gly Gln Trp Thr Tyr Gln Ile Tyr
1               5                   10                  15

<210> SEQ ID NO 77
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 77

Pro Pro Leu Val Lys Leu Trp Tyr Gln Leu Glu Lys Glu Pro Ile Val
1               5                   10                  15

Gly Ala

<210> SEQ ID NO 78
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 78

Ile His Leu Ala Leu Gln Asp Ser Gly Leu Glu Val Asn Ile Val
1               5                   10                  15

<210> SEQ ID NO 79
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 79

Val Tyr Leu Ala Trp Val Pro Ala His Lys Gly Ile Gly Gly Asn Glu
1               5                   10                  15

Gln Val

<210> SEQ ID NO 80
<211> LENGTH: 16
<212> TYPE: PRT
<213> ORGANISM: Artificial Sequence
<220> FEATURE:
<223> OTHER INFORMATION: OLP clade B consensus sequence

<400> SEQUENCE: 80

Ser Ala Gly Ile Arg Lys Val Leu Phe Leu Asp Gly Ile Asp Lys Ala
1               5                   10                  15

<210> SEQ ID NO 81
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 81

Thr Lys Glu Leu Gln Lys Gln Ile Thr Lys Ile Gln Asn Phe Arg Val
1               5                   10                  15

Tyr Tyr

<210> SEQ ID NO 82
<211> LENGTH: 18
<212> TYPE: PRT
<213> ORGANISM: Artificial Sequence
```

```
<220> FEATURE:
<223> OTHER INFORMATION: OLP clade B consensus sequence

<400> SEQUENCE: 82

Thr Lys Ile Gln Asn Phe Arg Val Tyr Tyr Arg Asp Ser Arg Asp Pro
1               5                   10                  15

Leu Trp

<210> SEQ ID NO 83
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 83

Tyr Tyr Arg Asp Ser Arg Asp Pro Leu Trp Lys Gly Pro Ala Lys Leu
1               5                   10                  15

Leu Trp

<210> SEQ ID NO 84
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 84

Lys Ile Ile Arg Asp Tyr Gly Lys Gln Met Ala Gly Asp Asp Cys Val
1               5                   10                  15

Ala

<210> SEQ ID NO 85
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 85

Gly Pro Gln Arg Glu Pro Tyr Asn Glu Trp Thr Leu Glu Leu Leu Glu
1               5                   10                  15

Glu Leu

<210> SEQ ID NO 86
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 86

Asp Leu Asn Asn Asn Thr Asn Thr Thr Ser Ser Ser Gly Glu Lys Met
1               5                   10                  15

Glu Lys

<210> SEQ ID NO 87
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 87
```

```
Ile Arg Asp Lys Val Gln Lys Glu Tyr Ala Leu Phe Tyr Lys Leu Asp
1               5                   10                  15

Val Val
```

<210> SEQ ID NO 88
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 88

```
Tyr Arg Leu Ile Ser Cys Asn Thr Ser Val Ile Thr Gln Ala Cys Pro
1               5                   10                  15

Lys Val
```

<210> SEQ ID NO 89
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 89

```
Ser Val Ile Thr Gln Ala Cys Pro Lys Val Ser Phe Glu Pro Ile Pro
1               5                   10                  15

Ile His
```

<210> SEQ ID NO 90
<211> LENGTH: 16
<212> TYPE: PRT
<213> ORGANISM: Artificial Sequence
<220> FEATURE:
<223> OTHER INFORMATION: OLP clade B consensus sequence

<400> SEQUENCE: 90

```
Thr Asn Val Ser Thr Val Gln Cys Thr His Gly Ile Arg Pro Val Val
1               5                   10                  15
```

<210> SEQ ID NO 91
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 91

```
Val Ala Pro Thr Lys Ala Lys Arg Arg Val Val Gln Arg Glu Lys Arg
1               5                   10                  15

Ala Val
```

<210> SEQ ID NO 92
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 92

```
Val Ile Glu Val Val Gln Arg Ala Cys Arg Ala Ile Leu His Ile Pro
1               5                   10                  15

Arg Arg
```

```
<210> SEQ ID NO 93
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 93

Val Lys His His Met Tyr Ile Ser Gly Lys Ala Lys Gly Trp Phe Tyr
1               5                   10                  15

Arg His

<210> SEQ ID NO 94
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 94

Gly Lys Ala Lys Gly Trp Phe Tyr Arg His His Tyr Glu Ser Thr His
1               5                   10                  15

Pro Arg

<210> SEQ ID NO 95
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 95

Thr Lys Leu Thr Glu Asp Arg Trp Asn Lys Pro Gln Lys Thr Lys Gly
1               5                   10                  15

His Arg

<210> SEQ ID NO 96
<211> LENGTH: 6
<212> TYPE: PRT
<213> ORGANISM: Artificial Sequence
<220> FEATURE:
<223> OTHER INFORMATION: Tag sequence

<400> SEQUENCE: 96

Ala His Gly His Arg Pro
1               5

<210> SEQ ID NO 97
<211> LENGTH: 14
<212> TYPE: PRT
<213> ORGANISM: Artificial Sequence
<220> FEATURE:
<223> OTHER INFORMATION: Tag sequence

<400> SEQUENCE: 97

Pro Ile His Asp His Asp His Pro His Leu Val Ile His Ser
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Tag sequence
<220> FEATURE:
```

```
<221> NAME/KEY: misc_feature
<222> LOCATION: (5)..(6)
<223> OTHER INFORMATION: Xaa can be any naturally occurring amino acid

<400> SEQUENCE: 98

Gly Met Thr Cys Xaa Xaa Cys
1               5

<210> SEQ ID NO 99
<211> LENGTH: 530
<212> TYPE: PRT
<213> ORGANISM: Artificial Sequence
<220> FEATURE:
<223> OTHER INFORMATION: HIV immunogen comprising OLPs

<400> SEQUENCE: 99
```

Glu Lys Ile Arg Leu Arg Pro Gly Gly Lys Lys Tyr Lys Leu Lys
1               5                   10                  15

His Ile Val Trp Ala Ser Arg Glu Leu Glu Arg Phe Ala Val Asn Pro
            20                  25                  30

Gly Leu Leu Glu Thr Ser Glu Gly Cys Arg Gln Ile Leu Gly Gln Leu
        35                  40                  45

Gln Pro Ser Leu Gln Thr Gly Ser Glu Glu Leu Lys Ser Leu Tyr Asn
    50                  55                  60

Thr Val Ala Thr Leu Tyr Cys Val His Gln Lys Ile Glu Val Ala Ala
65                  70                  75                  80

Ala Lys Ala Phe Ser Pro Glu Val Ile Pro Met Phe Ser Ala Leu Ala
                85                  90                  95

Ala Ala Gly His Gln Ala Ala Met Gln Met Leu Lys Glu Ala Ala Ala
            100                 105                 110

Ile Ala Pro Gly Gln Met Arg Glu Pro Arg Gly Ser Asp Ile Ala Gly
        115                 120                 125

Thr Thr Ser Thr Leu Gln Glu Gln Ile Gly Trp Met Thr Asn Asn Pro
    130                 135                 140

Pro Ile Pro Val Gly Glu Ile Tyr Lys Arg Trp Ile Ile Leu Gly Leu
145                 150                 155                 160

Asn Lys Ile Val Arg Met Tyr Ser Pro Thr Ser Ile Ala Ala Ala Tyr
                165                 170                 175

Val Asp Arg Phe Tyr Lys Thr Leu Arg Ala Glu Gln Ala Ala Ala Cys
            180                 185                 190

Gln Gly Val Gly Gly Pro Gly His Lys Ala Arg Val Leu Ala Ala Ala
        195                 200                 205

Cys Thr Glu Arg Gln Ala Asn Phe Leu Gly Lys Ile Trp Pro Ser His
    210                 215                 220

Lys Gly Arg Pro Gly Asn Phe Leu Gln Ser Arg Ala Ala Ala Lys Met
225                 230                 235                 240

Ile Gly Gly Ile Gly Gly Phe Ile Lys Val Arg Gln Tyr Asp Gln Ile
                245                 250                 255

Leu Ile Glu Ile Cys Gly His Lys Ala Ile Gly Thr Val Leu Val Gly
            260                 265                 270

Pro Thr Pro Val Asn Ile Ile Gly Arg Asn Leu Leu Thr Gln Ile Gly
        275                 280                 285

Cys Thr Leu Asn Phe Ala Ala Ala Leu Val Glu Ile Cys Thr Glu Met
    290                 295                 300

Glu Lys Glu Gly Lys Ile Ser Lys Ile Ala Ala Ala Leu Arg Trp Gly
305                 310                 315                 320

```
Phe Thr Thr Pro Asp Lys Lys His Gln Lys Glu Pro Pro Phe Leu Trp
                325                 330                 335
Met Gly Tyr Glu Leu His Pro Asp Lys Trp Thr Val Gln Pro Ile Val
            340                 345                 350
Leu Pro Glu Lys Asp Ser Trp Thr Val Asn Asp Ile Gln Lys Leu Val
        355                 360                 365
Gly Lys Leu Ala Ala Ala Ile Leu Lys Glu Pro Val His Gly Val Tyr
    370                 375                 380
Tyr Asp Pro Ser Lys Asp Leu Ile Ala Glu Ile Gln Lys Gln Gly Gln
385                 390                 395                 400
Gly Gln Trp Thr Tyr Gln Ile Tyr Ala Ala Thr Lys Glu Leu Gln
                405                 410                 415
Lys Gln Ile Thr Lys Ile Gln Asn Phe Arg Val Tyr Tyr Arg Asp Ser
                420                 425                 430
Arg Asp Pro Leu Trp Lys Gly Pro Ala Lys Leu Leu Trp Ala Ala Ala
            435                 440                 445
Lys Ile Ile Arg Asp Tyr Gly Lys Gln Met Ala Gly Asp Asp Cys Val
        450                 455                 460
Ala Ala Val Lys His His Met Tyr Ile Ser Lys Lys Ala Lys Gly
465                 470                 475                 480
Trp Phe Tyr Arg His His Tyr Glu Ser Thr His Pro Arg Ala Ala Ala
                485                 490                 495
Val Thr Lys Leu Thr Glu Asp Arg Trp Asn Lys Pro Gln Lys Thr Lys
                500                 505                 510
Gly His Arg Ala Ala Ala Trp Leu Glu Ala Gln Glu Glu Glu Val
            515                 520                 525
Gly Phe
    530

<210> SEQ ID NO 100
<211> LENGTH: 1587
<212> TYPE: DNA
<213> ORGANISM: Artificial Sequence
<220> FEATURE:
<223> OTHER INFORMATION: polynucleotide encoding immunogen comprising
      HIV OLPs

<400> SEQUENCE: 100
gagaagatcc ggctgcggcc aggcggaaag aagaagtaca agctgaagca catcgtctgg      60
gcctcgaggg agctggagcg gttcgcggtg aacccgggac ttctggagac gtcggagggg     120
tgcaggcaga tcctcggcca gctgcagccc tctctgcaaa cggggtctga ggagctgaag     180
agcctgtaca cacggtggc gaccctctac tgcgtccacc agaagatcga ggtggcagcg     240
gccaaggcgt tctcgccgga ggtcatcccc atgttctcgg cgctggcagc tgccggacac     300
caggccgcga tgcagatgct gaaggaggcc gctgcgatcg caccgggcca gatgagggag     360
ccacgcggtt ccgacatcgc gggaaccacc tcgacgctcc aggagcagat cggatggatg     420
acgaacaacc cgccaatccc ggtcggggag atctacaagc ggtggatcat cctcgggctg     480
aacaagatcg tccggatgta cagcccgacg tcgatcgctg cggcatacgt tgaccggttc     540
tacaagaccc tgagggccga gcaggcagcg gcctgccagg ggtcggtgg accagggcac     600 aaggcccgag tgctcgcggc cgcatgcacg gagcggcagg cgaacttcct ggggaagatc     660
tggccgtcgc acaagggccg accgggaaac ttcctccagt ctcgcgcagc ggctaagatg     720
atcggaggca tcggaggctt catcaaagtc cgtcagtacg accagatcct catcgagatc     780
```

```
tgcgggcaca aggcgatcgg aaccgtgctc gtcggcccaa cgcccgtgaa catcatcggc      840
cgcaacctgt taacgcagat cggctgcacc ctcaacttcg ccgcactagt ggagatctgc      900
acggagatgg agaaggaggg caagatatcg aagatcgcgg cagctctgag gtggggcttc      960
accacgccgg acaagaagca ccagaaggag ccgccattcc tgtggatggg atacgagctg     1020
caccgggaca gtggaccgt gcagcccatc gtcctgccgg agaaggactc gtggacggtg      1080
aacgacatcc agaagctcgt ggggaagctg gcggcagcca tcctcaagga gcccgtccac     1140
ggggtgtact acgacccctc taaggacctg atcgcggaga tccagaagca ggggcagggt     1200
cagtggacct accagatcta cgcagcagca accaaggagc tgcagaagca gatcacgaag     1260
atccagaact tccgcgtata ctaccgcgac tcgcgggacc ccctgtggaa gggccctgcg     1320
aagcttctct gggcagccgc gaagatcatc cgggactacg gcaagcagat ggcgggcgac     1380
gactgcgtgg ccgcagcggt gaagcaccat atgtacatct cgaagaaggc gaagggctgg     1440
ttctacagac accactacga gtccacccac cccagggcag ctgcggtgac gaagctgacg     1500
gaggaccggt ggaacaagcc ccagaagacg aagggtcacc gggcggctgc atggctggag     1560
gctcaggagg aggaggaggt gggcttc                                         1587
```

<210> SEQ ID NO 101
<211> LENGTH: 1593
<212> TYPE: DNA
<213> ORGANISM: Artificial Sequence
<220> FEATURE:
<223> OTHER INFORMATION: Polynucleotide encoding immunogen comprising
      HIV OLPs

<400> SEQUENCE: 101

```
gagaagatcc gcctgcgccc cggcggcaag aaaaagtaca agctgaagca catcgtgtgg       60
gcctcccgcg agctggagcg cttcgccgtg aaccccggcc tgctggagac ctccgagggc      120
tgccgccaga tcctgggcca gctgcagccc tccctgcaga ccggctccga ggagctgaag      180
tccctgtaca acaccgtggc caccctgtac tgcgtgcaca gaagatcga ggtggccgcc      240 gccaaggcct ctcccccga ggtgatcccc atgttctccg ccctggccgc cgccggccac      300
caggccgcca tgcagatgct gaaggaggcc gccgccatcg cccccggcca gatgcgcgag      360
ccccgcggct ccgacatcgc cggcaccacc tccaccctgc aggagcagat cggctggatg      420
accaacaacc cccccatccc cgtgggcgag atctacaagc gctggatcat cctgggcctg      480
aacaagatcg tgcgcatgta ctccccccac ctccatcgccg ccgcctacgt ggaccgcttc      540
tacaagaccc tgcgcgccga gcaggccgcc gcctgccagg gcgtgggcgg ccccggccac      600
aaggcccgcg tgctggccgc cgcctgcacc gagcgccagg ccaacttcct gggcaagatc      660
tggccctccc acaagggccg cccggcaac ttcctgcagt cccgcgccgc cgccaagatg      720
atcggcggca tcggcggctt catcaaggtg cgccagtacg accagatcct gatcgagatc      780 tgcgccaca aggccatcgg caccgtgctg gtgggcccca cccccgtgaa catcatcggc      840
cgcaacctgc tgaccagat cggctgcacc ctgaacttcg ccgccctggt ggagatctgc      900
accgagatgg agaaggaggg caagatctcc aagatcgccg ccgccctgcg ctggggcttc      960
accacccccg acaagaagca ccagaaggag ccccccttcc tgtggatggg ctacgagctg     1020
caccccgaca gtggaccgt gcagcccatc gtgctgcccg agaaggactc ctggaccgtg      1080
aacgacatcc agaagctggt ggggcaagctg gccgccgcca tcctgaagga gcccgtgcac     1140
ggcgtgtact acgacccctc caaggacctg atcgccgaga tccagaagca gggccagggc     1200
```

```
cagtggacct accagatcta cgccgccgcc accaaggagc tgcagaagca gatcaccaag    1260
atccagaact tccgcgtgta ctaccgcgac tcccgcgacc ccctgtggaa gggcccccgcc   1320 aagctgctgt gggccgccgc caagatcatc cgcgactacg gcaagcagat ggccggcgac    1380
gactgcgtgg ccgccgccgt gaagcaccac atgtacatct ccaagaaggc caagggctgg   1440
ttctaccgcc accactacga gtccacccac cccgcgccg ccgccgtgac caagctgacc    1500
gaggaccgct ggaacaagcc ccagaagacc aagggccacc gcgccgccgc ctggctggag   1560
gcccaggagg aggaagaggt gggcttctga tag                                 1593
```

PRIME/BOOST IMMUNIZATION REGIMEN AGAINST HIV-1 UTILIZING A MULTIEPITOPE T CELL IMMUNOGEN COMPRISING GAG, POL, VIF, AND NEF EPITOPES

RELATED APPLICATIONS

This application claims priority to U.S. Provisional Appl. No. 62/935,519, filed Nov. 14, 2019, which is incorporated herein by reference in its entirety.

REFERENCE TO SEQUENCE LISTING SUBMITTED ELECTRONICALLY

The content of the electronically submitted Sequence Listing ("3834_0070001_Seqlisting_ST25"; Size: 45,669 bytes; and Date of Creation: Oct. 13, 2020) filed with the application is incorporated herein by reference in its entirety.

FIELD OF THE INVENTION

The present invention relates to immunogenic therapies for the treatment or prevention of a human immunodeficiency virus (HIV) infection or a disease associated with an HIV infection.

BACKGROUND OF THE INVENTION

Increased access to highly active combination antiretroviral therapy (cART) has resulted in a dramatic decrease in morbidity and mortality associated with infection by HIV. However, despite having new classes of antiretroviral drugs, currently available cART regimens are not able to eradicate HIV from the body. Consequently, cART cessation in participants maintaining undetectable viral load is followed by a fast rebound in viremia. Moltó et al., AIDS Res Hum Retroviruses. 2004; 20 (12):1283-8; El-Sadr et al., N Engl J Med. 2006; 355 (22):2283-96. This reflects the inability of the standard cART in eliminating a viral reservoir formed by latently infected cells in which the integrated provirus remains quiescent and stable in early stages of infection, and the inability of the immune response to effectively contain viral rebound after treatment interruption.

Even though cART results in control of the viral load (thus preventing the development of AIDS and virus transmission), it has several shortcomings:

1. Not curative: cART are treatments for life. If a person stops the treatment, even for a short period of time, the viral load rebounds to initial levels within 2-4 weeks, making this person infective again.

2. Adherence issues: 30 to 50% of patients are not able to control the viral load, because they don't follow the treatment regime rigorously enough. This has much to do with psychological stress—living with HIV with no cure in sight affects a patient's quality of life—and even without that, all patients are inconvenienced by their treatment routines, to varying degrees ("pill fatigue").

3. Resistance: HIV can develop resistance to cART.

4. Side-effects: Because of the high long-term toxicity of cART, patients suffer from serious adverse events, such as cardiovascular diseases, dyslipidemias, hypertension, diabetes, osteoporosis, and kidney diseases.

5. High and permanent cost: Treating a patient with cART costs about €20.000 per year, while the total cost for the health system during the patient life time is calculated to be €400.000.

6. Social stigma: The stigma surrounding HIV makes people reluctant to get tested, or to disclose their HIV status; it also limits their access to available HIV treatment.

Thus, an HIV-treatment to achieve sustained viral control without continuous cART is desirable.

Multiple strategies have been evaluated to try to achieve an optimal control of HIV infection in the absence of cART. These have included early treatment initiation within the first 6 months after HIV acquisition, cART intensification, immunotherapies including interleukin administrations (IL-2, IL-7, IL-10, IL-12, and IL-15), treatment with cyclosporine, mycophenolate, hydroxyurea, thalidomide, passive administration of antibodies, etc. and a wide range of therapeutic vaccines designed to expand the response mediated by cytotoxic T lymphocytes. Buzón et al., Nat Med. 2010; 16 (4):460-5; Autran et al., AIDS. 2008; 22 (11):1313-22; Schooley et al., J Infect Dis. 2010; 202 (5):705-16; Harrer et al., Vaccine. 2014; 32 (22):2657-65.

Minimal clinical effect has been observed after a vaccination strategy with an autologous dendritic-cell vaccination approach, which was able to demonstrate transient 1 log reduction in the viral setpoint of vaccinated compared to unvaccinated patients after discontinuation of treatment. García et al., Sci Transl Med. 2013; 5 (166):166ra2. In addition, recent data from a pilot study suggests that re-education of T cells towards conserved regions of HIV by therapeutic vaccines in early treated patients (<6 months of HIV acquisition) may contribute to durable HIV control in a considerable proportion of participants after treatment cessation. Mothe et al., CROI 2017, 119LB. Both sets of results set the stage for improved therapeutic vaccine concepts.

An important cause of a therapeutic vaccine's failure is the composition of the antigen insert (immunogen) expressed in the vectors, the combinations thereof used for the administration of the vaccine, and in the dosing regimen of the vaccine components to be administered. In particular, the inclusion of whole HIV proteins as antigens limits the immunogenic effect of the vaccine towards a nonspecific cytotoxic T lymphocyte (CTL) expansion: a CTL response pattern which, in natural HIV infection, has been shown ineffective in controlling viral replication in most individuals. Mothe et al., J Transl Med. 2011; 9 (1):208; Pereyra et al., J Virol. 2014; 88 (22):12937-48.

In this regard, there is a need to improve the immunogen design by selecting viral sequences able to induce T cell responses which are more beneficial to the host. Létourneau et al., PLoS One. 2007; 2 (10):e984; Rolland et al., PLoS Pathogens. 2007; 3:1551-5; Mothe et al., J Transl Med. 2015; 13 (1):60.

Moreover, HIV-1 infection induces strong and broadly directed HLA class I and class II restricted T-cell responses, for which some specific epitopes and restricting HLA alleles have been associated with relative in vivo virus control or lack thereof. Brander et al., Curr Opin Immunol. 2006; 18 (4):430-7; Zuñiga et al., Virol. 2006; 80 (6):3122-5; Frahm et al., Nat Immunol. 2006; 7 (2):173-8. Among these, CD8+ CTL responses to HIV-1 Gag have most consistently been associated with reduced viral loads in both HIV-1 clade B- and C-infected cohorts. Zuñiga et al., Virol. 2006; 80 (6): 3122-5; Kiepiela et al., Nat Med. 2007; 13 (1):46-53. CD4+ T-cell responses to Gag have also been associated with relative HIV-1 control. Ranasinghe et al., J Virol. 2012; 86 (1):277-83; Ranasinghe et al., Nat Med. 2013; 19 (7):930-3. In addition, the elevated level of conservation of Gag across viral isolates and the severe fitness reductions caused by CTL escape variants may provide Gag-specific T-cell responses with a particular advantage.

At the same time, it is also clear that not all Gag-specific responses exert the same antiviral activity, suggesting that a rational selection of Gag components could help focus vaccine induced responses onto the most protective targets. The same likely applies for all other viral proteins as well, as they may contain some regions that are of particular value for inclusion in a vaccine while other regions or proteins may induce less useful T cell responses. As such, effective vaccine design should likely aim to induce broad and evenly distributed responses to conserved and vulnerable sites of the virus while avoiding the induction of responses to regions that can be highly immunogenic but that may act as potential "decoy" targets and divert responses away from more relevant targets. Rolland et al., PLoS Pathogens. 2007; 3:1551-5; Kulkarni et al., PLoS One. 2013; 8 (3):e60245; Kulkarni et al., PLoS One. 2014; 9 (1):e86254; Dinges et al., J Virol. 2010; 84 (9):4461-8; Kunwar et al., PLoS One. 2013; 8 (5):e64405; Niu et al., Vaccine. 2011; 29 (11):2110-9.

Moreover, there is also a need to develop a preventive vaccine that protects human beings from an HIV infection. Although new HIV infections have been reduced by 40% since the peak in 1997, in 2018 alone around 1.7 million were newly infected with HIV.

This goal has proven to be elusive. Of the efficacy trials of HIV vaccines that have been reported thus far, only one has shown a modest relative reduction of 31% in HIV infections in a general Thai population. Rerks-Ngarm S, Pitisuttithum P, Nitayaphan S, et al., N Engl J Med. 2009; 361:2209-2220.

The failure of various T-cell vaccine candidates expressing entire HIV-1 proteins in large human clinical trials and data from post-trial analyses suggests a sieve effect on the infecting viral strains and indicates there is a need to improve vaccine immunogen design. Buchbinder et al., Lancet. 2008; 372 (9653):1881-93; Rerks-Ngarm et al., N Engl J Med. 2009; 361 (23):2209-20; Hammer et al., N Engl J Med. 2013; 369 (22):2083-92; Rolland et al., Nat Med. 2011; 17 (3):366-71.

SUMMARY OF THE INVENTION

In one embodiment, the present invention is directed to a method of inducing an immune response against a human immunodeficiency virus (HIV) in a subject in need thereof (e.g., an HIV-infected human), comprising (a) administering to the subject 1 to 10 administrations of an immunogenically effective amount of a first viral vector encoding an immunogenic polypeptide; and (b) administering to the subject 1 to 10 administrations of an immunogenically effective amount of a second viral vector encoding the immunogenic polypeptide; wherein the immunogenic polypeptide comprises:

(i) a sequence having at least 90% identity to the sequence of SEQ ID NO:1, (ii) a sequence having at least 90% identity to the sequence of SEQ ID NO:2, (iii) a sequence having at least 90% identity to the sequence of SEQ ID NO:3, (iv) a sequence having at least 90% identity to the sequence of SEQ ID NO:4, (v) a sequence having at least 90% identity to the sequence of SEQ ID NO:5, (vi) a sequence having at least 90% identity to the sequence of SEQ ID NO:6, (vii) a sequence having at least 90% identity to the sequence of SEQ ID NO:7, (viii) a sequence having at least 90% identity to the sequence of SEQ ID NO:8, (ix) a sequence having at least 90% identity to the sequence of SEQ ID NO:9, (x) a sequence having at least 90% identity to the sequence of SEQ ID NO:10, (xi) a sequence having at least 90% identity to the sequence of SEQ ID NO:11, (xii) a sequence having at least 90% identity to the sequence of SEQ ID NO:12, (xiii) a sequence having at least 90% identity to the sequence of SEQ ID NO:13, (xiv) a sequence having at least 90% identity to the sequence of SEQ ID NO:14, (xv) a sequence having at least 90% identity to the sequence of SEQ ID NO:15, and (xvi) a sequence having at least 90% identity to the sequence of SEQ ID NO:16.

In one embodiment, the method comprises at least 2, at least 3, at least 4, at least 5 at least 6, at least 7, at least 8, or at least 9 administrations of the first viral vector and/or at least 2, at least 3, at least 4, at least 5, at least 6, at least 7, at least 8, or at least 9 administrations of the second viral vector. In some embodiments, the immunogenic polypeptide comprises:

(i) a sequence having at least 90%, at least 95%, at least 96%, at least 97%, at least 98%, or at least 99% identity to the sequence of SEQ ID NO:1, (ii) a sequence having at least 90%, at least 95%, at least 96%, at least 97%, at least 98%, or at least 99% identity to the sequence of SEQ ID NO:2, (iii) a sequence having at least 90%, at least 95%, at least 96%, at least 97%, at least 98%, or at least 99% identity to the sequence of SEQ ID NO:3, (iv) a sequence having at least 90%, at least 95%, at least 96%, at least 97%, at least 98%, or at least 99% identity to the sequence of SEQ ID NO:4, (v) a sequence having at least 90%, at least 95%, at least 96%, at least 97%, at least 98%, or at least 99% identity to the sequence of SEQ ID NO:5, (vi) a sequence having at least 90%, at least 95%, at least 96%, at least 97%, at least 98%, or at least 99% identity to the sequence of SEQ ID NO:6, (vii) a sequence having at least 90%, at least 95%, at least 96%, at least 97%, at least 98%, or at least 99% identity to the sequence of SEQ ID NO:7, (viii) a sequence having at least 90%, at least 95%, at least 96%, at least 97%, at least 98%, or at least 99% identity to the sequence of SEQ ID NO:8, (ix) a sequence having at least 90%, at least 95%, at least 96%, at least 97%, at least 98%, or at least 99% identity to the sequence of SEQ ID NO:9, (x) a sequence having at least 90%, at least 95%, at least 96%, at least 97%, at least 98%, or at least 99% identity to the sequence of SEQ ID NO:10, (xi) a sequence having at least 90%, at least 95%, at least 96%, at least 97%, at least 98%, or at least 99% identity to the sequence of SEQ ID NO:11, (xii) a sequence having at least 90%, at least 95%, at least 96%, at least 97%, at least 98%, or at least 99% identity to the sequence of SEQ ID NO:12, (xiii) a sequence having at least 90%, at least 95%, at least 96%, at least 97%, at least 98%, or at least 99% identity to the sequence of SEQ ID NO:13, (xiv) a sequence having at least 90%, at least 95%, at least 96%, at least 97%, at least 98%, or at least 99% identity to the sequence of SEQ ID NO:14, (xv) a sequence having at least 90%, at least 95%, at least 96%, at least 97%, at least 98%, or at least 99% identity to the sequence of SEQ ID NO:15, and (xvi) a sequence having at least 90%, at least 95%, at least 96%, at least 97%, at least 98%, or at least 99% identity to the sequence of SEQ ID NO:16.

In one embodiment, the present invention relates to a method of treating or preventing a human immunodeficiency virus (HIV) infection, or a disease associated with an HIV infection, in a subject in need thereof, comprising (a) administering to the subject 1 to 10 administrations of an immunogenically effective amount of a first viral vector encoding the immunogenic polypeptide; and (b) administering to the subject 1 to 10 administrations of an immunogenically effective amount of a second viral vector encoding the immunogenic polypeptide; wherein the immunogenic polypeptide comprises:

(i) a sequence having at least 90% identity to the sequence of SEQ ID NO:1, (ii) a sequence having at least 90% identity to the sequence of SEQ ID NO:2, (iii) a sequence having at least 90% identity to the sequence of SEQ ID NO:3, (iv) a sequence having at least 90% identity to the sequence of SEQ ID NO:4, (v) a sequence having at least 90% identity to the sequence of SEQ ID NO:5, (vi) a sequence having at least 90% identity to the sequence of SEQ ID NO:6, (vii) a sequence having at least 90% identity to the sequence of SEQ ID NO:7, (viii) a sequence having at least 90% identity to the sequence of SEQ ID NO:8, (ix) a sequence having at least 90% identity to the sequence of SEQ ID NO:9, (x) a sequence having at least 90% identity to the sequence of SEQ ID NO:10, (xi) a sequence having at least 90% identity to the sequence of SEQ ID NO:11, (xii) a sequence having at least 90% identity to the sequence of SEQ ID NO:12, (xiii) a sequence having at least 90% identity to the sequence of SEQ ID NO:13, (xiv) a sequence having at least 90% identity to the sequence of SEQ ID NO:14, (xv) a sequence having at least 90% identity to the sequence of SEQ ID NO:15, and (xvi) a sequence having at least 90% identity to the sequence of SEQ ID NO:16.

In one embodiment, this method comprises at least 2, at least 3, at least 4, at least 5 at least 6, at least 7, at least 8, or at least 9 administrations of the first viral vector and/or at least 2, at least 3, at least 4, at least 5 at least 6, at least 7, at least 8, or at least 9 administrations of the second viral vector. In another embodiment, the immunogenic polypeptide comprises:

(i) a sequence having at least 90%, at least 95%, at least 96%, at least 97%, at least 98%, or at least 99% identity to the sequence of SEQ ID NO:1, (ii) a sequence having at least 90%, at least 95%, at least 96%, at least 97%, at least 98%, or at least 99% identity to the sequence of SEQ ID NO:2, (iii) a sequence having at least 90%, at least 95%, at least 96%, at least 97%, at least 98%, or at least 99% identity to the sequence of SEQ ID NO:3, (iv) a sequence having at least 90%, at least 95%, at least 96%, at least 97%, at least 98%, or at least 99% identity to the sequence of SEQ ID NO:4, (v) a sequence having at least 90%, at least 95%, at least 96%, at least 97%, at least 98%, or at least 99% identity to the sequence of SEQ ID NO:5, (vi) a sequence having at least 90%, at least 95%, at least 96%, at least 97%, at least 98%, or at least 99% identity to the sequence of SEQ ID NO:6, (vii) a sequence having at least 90%, at least 95%, at least 96%, at least 97%, at least 98%, or at least 99% identity to the sequence of SEQ ID NO:7, (viii) a sequence having at least 90%, at least 95%, at least 96%, at least 97%, at least 98%, or at least 99% identity to the sequence of SEQ ID NO:8, (ix) a sequence having at least 90%, at least 95%, at least 96%, at least 97%, at least 98%, or at least 99% identity to the sequence of SEQ ID NO:9, (x) a sequence having at least 90%, at least 95%, at least 96%, at least 97%, at least 98%, or at least 99% identity to the sequence of SEQ ID NO:10, (xi) a sequence having at least 90%, at least 95%, at least 96%, at least 97%, at least 98%, or at least 99% identity to the sequence of SEQ ID NO:11, (xii) a sequence having at least 90%, at least 95%, at least 96%, at least 97%, at least 98%, or at least 99% identity to the sequence of SEQ ID NO:12, (xiii) a sequence having at least 90%, at least 95%, at least 96%, at least 97%, at least 98%, or at least 99% identity to the sequence of SEQ ID NO:13, (xiv) a sequence having at least 90%, at least 95%, at least 96%, at least 97%, at least 98%, or at least 99% identity to the sequence of SEQ ID NO:14, (xv) a sequence having at least 90%, at least 95%, at least 96%, at least 97%, at least 98%, or at least 99% identity to the sequence of SEQ ID NO:15, and (xvi) a sequence having at least 90%, at least 95%, at least 96%, at least 97%, at least 98%, or at least 99% identity to the sequence of SEQ ID NO:16.

In some embodiments, the present invention relates to a method of treating or preventing an HIV infection or a disease associated with an HIV infection in a subject in need thereof, comprising (a) administering to the subject 1 to 5 administrations of an immunogenically effective amount of first viral vector encoding an immunogenic polypeptide; and (b) administering to the subject 1 to 5 administrations of an immunogenically effective amount of a second viral vector encoding the immunogenic polypeptide; wherein the immunogenic polypeptide comprises:

(i) a sequence having at least 90% identity to the sequence of SEQ ID NO:1, (ii) a sequence having at least 90% identity to the sequence of SEQ ID NO:2, (iii) a sequence having at least 90% identity to the sequence of SEQ ID NO:3, (iv) a sequence having at least 90% identity to the sequence of SEQ ID NO:4, (v) a sequence having at least 90% identity to the sequence of SEQ ID NO:5, (vi) a sequence having at least 90% identity to the sequence of SEQ ID NO:6, (vii) a sequence having at least 90% identity to the sequence of SEQ ID NO:7, (viii) a sequence having at least 90% identity to the sequence of SEQ ID NO:8, (ix) a sequence having at least 90% identity to the sequence of SEQ ID NO:9, (x) a sequence having at least 90% identity to the sequence of SEQ ID NO:10, (xi) a sequence having at least 90% identity to the sequence of SEQ ID NO:11, (xii) a sequence having at least 90% identity to the sequence of SEQ ID NO:12, (xiii) a sequence having at least 90% identity to the sequence of SEQ ID NO:13, (xiv) a sequence having at least 90% identity to the sequence of SEQ ID NO:14, (xv) a sequence having at least 90% identity to the sequence of SEQ ID NO:15, and (xvi) a sequence having at least 90% identity to the sequence of SEQ ID NO:16.

DETAILED DESCRIPTION OF THE INVENTION

Figure 1:
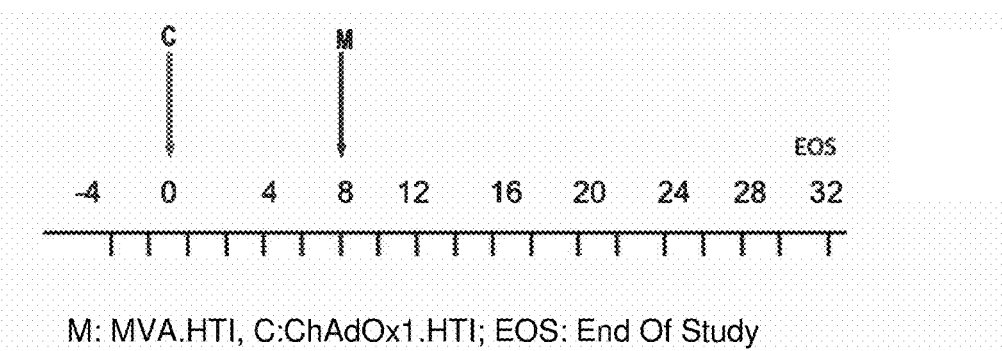
FIG. 1 shows a study to demonstrate the safety and immunogenicity of a prime/boost strategy of the present invention in HIV-1 negative individuals.
Figure 2:
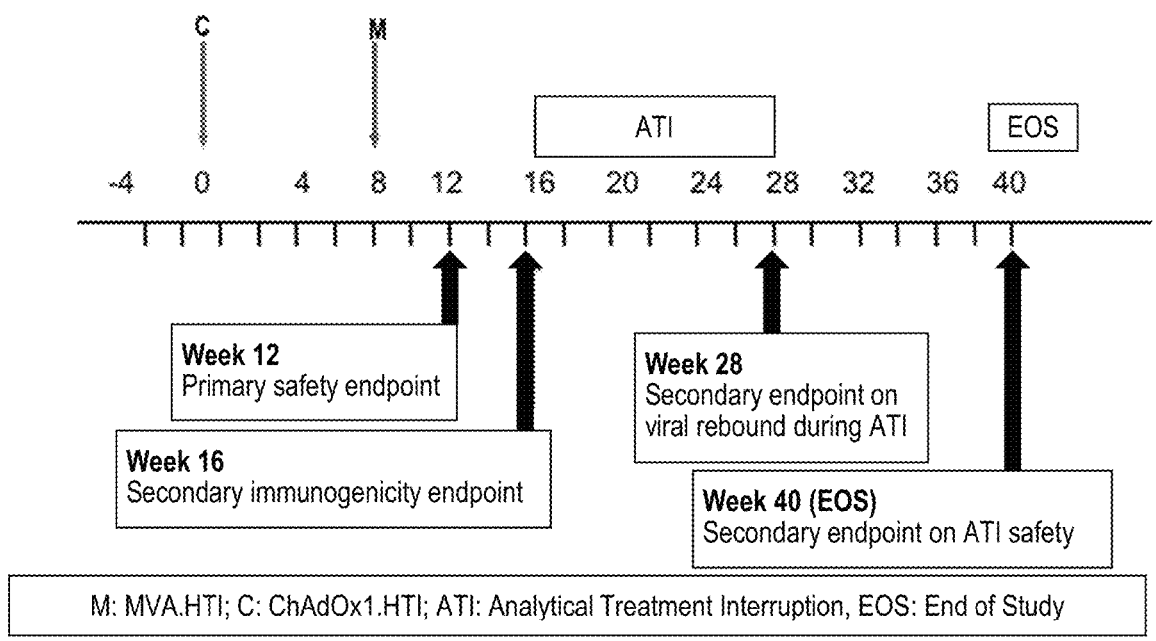
FIG. 2 shows a study to demonstrate the safety and efficacy of a prime/boost strategy of the present invention in HIV-1 positive individuals.

The present invention is directed to methods of treating or preventing a human immunodeficiency virus (HIV) infection or a disease associated with an HIV infection in a subject in need thereof by administering an immunogenically effective amount of an HIV immunogen termed HTI.

Definitions

The term "adjuvant", as used herein, refers to an immunological agent that modifies the effect of an immunogen, while having few if any direct effects when administered by itself. It is often included in vaccines to enhance the recipient's immune response to a supplied antigen, while keeping the injected foreign material to a minimum. Adjuvants are added to vaccines to stimulate the immune system's response to the target antigen, but do not in themselves confer immunity. Non-limiting examples of useful adjuvants include mineral salts, polynucleotides, polyarginines, ISCOMs, saponins, monophosphoryl lipid A, imiquimod, CCR-5 inhibitors, toxins, polyphosphazenes, cytokines, immunoregulatory proteins, immunostimulatory fusion proteins, co-stimulatory molecules, and combinations thereof. Mineral salts include, but are not limited to, $AIK(SO_4)_2$, $AlNa(SO_4)_2$, $AlNH(SO_4)_2$, silica, alum, $Al(OH)_3$, $Ca_3(PO_4)_2$, kaolin, or carbon. Useful immunostimulatory polynucleotides include, but are not limited to, CpG oligonucleotides with or without immune stimulating complexes (ISCOMs), CpG oligonucleotides with or without polyarginine, poly IC or poly AU acids. Toxins include cholera toxin. Saponins include, but are not limited to, QS21, QS17 or QS7. An example of a useful immunostimulatory fusion protein is the fusion protein of IL-2 with the Fc fragment of immunoglobulin. Useful immunoregulatory molecules include, but are not limited to, CD40L and CD1a ligand. Cytokines useful as adjuvants include, but are not limited to, IL-1, IL-2, IL-4, GMCSF, IL-12, IL-15, IGF-1, IFNα, IFN-β, and interferon gamma. Also, examples are of muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2 percent squalene/TWEEN® 80 emulsion, lipopolysaccharides and its various derivatives, including lipid A, Freund's Complete Adjuvant (FCA), Freund's Incomplete Adjuvants, Merck Adjuvant 65, polynucleotides (e.g., poly IC and poly AU acids), wax D from *Mycobacterium tuberculosis*, substances found in *Corynebacterium parvum, Bordetella pertussis*, and members of the genus *Brucella*, Titermax, Quil A, ALUN, Lipid A derivatives, choleratoxin derivatives, HSP derivatives, LPS derivatives, synthetic peptide matrixes or GMDP, Montanide ISA-51 and QS-21, CpG oligonucleotide, poly I:C, and GMCSF. See Osol A., Ed., Remington's Pharmaceutical Sciences (Mack Publishing Co., Easton, Pa., US, 1980, pp. 1324-1341), Hunter R, U.S. Pat. No. 5,554,372, and Jager E, Knuth A, WO1997028816. Combinations of adjuvants can also be used.

The term "AIDS", as used herein, refers to the symptomatic phase of HIV infection, and includes both Acquired Immune Deficiency Syndrome (commonly known as AIDS) and "ARC," or AIDS-Related Complex. Adler et al., Brit. Med. J. 1987; 294: 1145-1147. The immunological and clinical manifestations of AIDS are well known in the art and include, for example, opportunistic infections and cancers resulting from immune deficiency.

The term "amino acid linker", as used herein, refers to an amino acid sequence other than that appearing at a particular position in the natural protein and is generally designed to be flexible or to interpose a structure, such as an α-helix, between two protein moieties. A linker is also referred to as a spacer. The linker is typically non-antigenic and can be of essentially any length (e.g., 2, 3, 4, 5, 6, 7, 8, 9, 10, 11, 12, 13, 14, 15, 16, 17, 18, 19, 20, or more amino acids). The linker may also be a location or sequence where the cellular antigen processing machinery can initiate the degradation of the immunogenic polypeptide without destroying potent T cell epitopes).

The term "codon optimized", as used herein, relates to the alteration of codons in nucleic acid molecules to reflect the typical codon usage of the host organism without altering the polypeptide encoded by the DNA for the purpose of improve expression. A plethora of methods and software tools for codon optimization have been reported previously. Narum et al., Infect. Immun. 2001; 69 (12):7250-7253, Outchkourov et al., Protein Expr. Purif. 2002; 24 (1):18-24, Feng L, et al., Biochemistry 2000; 39 (50):15399-15409, and Humphreys et al., Protein Expr. Purif. 2000; 20 (2):252-2.

The terms "comprising" or "comprises", as used herein, encompass also "consisting of" and "consisting essentially of" according to the generally accepted patent practice.

The expression "disease associated with a HIV infection", as used herein, includes a state in which the subject has developed AIDS, but also includes a state in which the subject infected with HIV has not shown any sign or symptom of the disease. Thus, the vaccine of the invention when administered to a subject that has no clinical signs of the infection can have a preventive activity, since they can prevent the onset of the disease. The immunogenic compositions are capable of preventing or slowing the infection and destruction of healthy CD4+ T cells in such a subject. It also refers to the prevention and slowing the onset of symptoms of the acquired immunodeficiency disease such as extreme low CD4+ T cell count and repeated infections by opportunistic pathogens such as *Mycobacteria* spp., *Pneumocystis carinii*, and *Pneumocystis cryptococcus*. Beneficial or desired clinical results include, but are not limited to, an increase in absolute naive CD4+ T cell count (range 10-3520), an increase in the percentage of CD4+ T cell over total circulating immune cells (range 1-50 percent), and/or an increase in CD4+ T cell count as a percentage of normal CD4+ T cell count in an uninfected subject (range 1-161 percent).

The terms "variant" and "fragment", as used herein, refer to a polypeptide derived from any of SEQ ID NOs:1-16 by deletion of one or more terminal amino acids at the N-terminus or at the C-terminus of an individual SEQ ID NO. Variant or fragments preferably have a length of at least 8 amino acids or up to 10%, up to 20%, up to 30%, up to 40%, up to 50%, up to 60%, up to 70%, up to 80%, up to 90%, or up to 99% of its respective SEQ ID NO.

The terms "HTI" and "HTI immunogen" refer to the immunogenic polypeptide identified as HTI and disclosed in U.S. Pat. No. 9,988,425 (the entire contents of which are hereby incorporated by reference).

The term "human immunodeficiency virus" or "HIV", as used herein, refers to human immunodeficiency viruses generically and includes HIV type 1 ("HIV-1"), HIV type 2 ("HIV-2") or other HIV viruses, including, for example, the HIV-1, HIV-2, emerging HIV and other HIV subtypes and HIV variants, such as widely dispersed or geographically isolated variants and simian immunodeficiency virus ("SIV"). For example, an ancestral viral gene sequence can be determined for the env and gag genes of HIV-1, such as for HIV-1 subtypes A, B, C, D, E, F, G, H, J, and K, and intersubtype recombinants such as AG, AGI, and for groups M, N, O or for HIV-2 viruses or HIV-2 subtypes A or B. HIV-1, HIV-2 and SIV include, but are not limited to, extracellular virus particles and the forms of the viruses associated with their respective infected cells.

The term "inducing an immune response" as used herein is intended to mean causing a desired immune response or effect in a subject in need thereof against an infection, such as HIV infection, preferably for therapeutic purposes. The term encompasses providing a therapeutic immunity for treating against a pathogenic agent, e.g., HIV. In one embodiment, the term refers to causing or improving cellular immunity, e.g., T cell response, against HIV infection. Typically, the administration of the primer and booster vaccine compositions of the invention will have a therapeutic aim to generate an immune response against HIV after HIV infection or development of symptoms characteristic of HIV infection.

The term "immunogenically effective amount" as used herein is intended to mean an amount of an immunogenic composition, e.g., a vector encoding an immunogenic polypeptide such as the HTI immunogen, sufficient to induce a desired immune effect or immune response in a subject in need thereof. In one embodiment, an immunogenically effective amount means an amount sufficient to induce an immune response in a subject in need thereof. In another embodiment, an immunologically effective amount means an amount sufficient to produce immunity in a subject in need thereof, e.g., provide a therapeutic effect against a disease such as HIV infection. An immunologically effective amount can vary depending upon a variety of factors, such as the physical condition of the subject, age, weight, health, etc. An immunologically effective amount can readily be determined by one of ordinary skill in the art in view of the present disclosure.

The term "operably linked", as used herein, is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). See Auer H, Nature Biotechnol. 2006; 24: 41-43.

The term "peptide tag" or "tag", as used herein, refers to a peptide or amino acid sequence, which can be used in the isolation or purification of said immunogen. Thus, said tag is capable of binding to one or more ligands, for example, one or more ligands of an affinity matrix such as a chromatography support or bead with high affinity. Illustrative, non-limitative, examples of tags useful for isolating or purifying a protein include Arg-tag, FLAG-tag, His-tag, or Strep-tag; an epitope capable of being recognized by an antibody, such as c-myc-tag (recognized by an anti-c-myc antibody), SBP-tag, S-tag, calmodulin binding peptide, cellulose binding domain, chitin binding domain, glutathione S-transferase-tag, maltose binding protein, NusA, TrxA, DsbA or Avi-tag; an amino acid sequence, such as AHGHRP (SEQ ID NO:53), PIHDHDHPHLVIHS (SEQ ID NO:54), or GMTCXXC (SEQ ID NO:55); or β-galactosidase. Terpe et al., Appl. Microbiol. Biotechnol. 2003; 60:523-525.

The term "secretion signal peptide" refers to a highly hydrophobic amino acid sequence (e.g., preferably 15 to 60 amino acids long) of proteins that must cross through membranes to arrive at their functioning cellular location. By binding to signal recognition particles, these sequences direct nascent protein-ribosome complexes to a membrane where the protein is inserted during translation. Signal peptides direct translational uptake of the protein by various membranes (e.g., endoplasmic reticulum, mitochondria, chloroplast, peroxisome). Leader signal sequences on non-membrane proteins are ultimately removed by specific peptidases. Some signal peptides used include MCP-3 chemokine, for promoting secretion and attraction of antigen presenting cells; a catenin (CATE)-derived peptide for increased proteasomal degradation; and the lysosomal associated protein, LAMP1 for targeting the MHC II compartment. Rosati et al., Proc. Natl. Acad. Sci. USA 2009; 106:15831-15836.

The expression "sequential administration", as used herein, means that the administration is not simultaneous, but a first administration is performed, followed by one or more successive administrations.

The terms "prevent," "preventing," and "prevention", as used herein, refer to inhibiting the inception or decreasing the occurrence of a disease in an animal. Prevention may be complete (e.g., the total absence of pathological cells in a subject). The prevention may also be partial, such that for example the occurrence of pathological cells in a subject is less than that which would have occurred without the present invention. Prevention also refers to reduced susceptibility to a clinical condition.

The term "treat" or "treatment", as used herein, refers to the administration of an immunogenic composition of the invention or of a medicament containing it to control the progression of the disease before or after clinical signs have appeared. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state and remission (both partial and total). The control of progression of the disease also involves an extension of survival, compared with the expected survival if treatment was not applied.

The term "vaccine", as used herein, refers to a substance or composition that establishes or improves immunity to a particular disease in a subject by inducing an adaptive immune response including an immunological memory. A vaccine typically contains an agent that resembles a disease-causing microorganism or a part thereof (e.g., a polypeptide). Vaccines can be prophylactic or therapeutic.

The term "vector", as used herein, refers either a nucleic acid molecule or viral vector "comprising", "containing" or "encoding", as used herein, an immunogenic polypeptide described herein (e.g., the HTI immunogen). For example, a vector includes, but is not limited to, a nucleic acid vector (e.g., a nucleic acid molecule, linear or circular, operably linked to additional segments that provide for its autonomous replication in a host cell of interest or according to the expression cassette of interest). A vector also includes, but is not limited to, a viral vector "comprising", "containing" or "encoding", as used herein, an immunogenic polypeptide or nucleic acid molecule encoding an immunogenic polypeptide.

The term "virologic suppression" in relation to an HIV-infected human means maintenance in the human of a measurable HIV viral load of less than 2000 copies of HIV RNA per mL of blood or plasma, for example, less than 1000 copies/mL, less than 500 copies/mL, less than 100 copies/mL, less than 50 copies mL, less than 40 copies mL, less than 30 copies mL, or less than 20 copies/mL.

As used in the present disclosure and claims, the singular forms "a", "an", and "the" include plural forms unless the context clearly dictates otherwise.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Methods of Treating or Preventing an HIV Infection or a Disease Associated with an HIV Infection In general terms, the present invention is directed to a method of treating or preventing an HIV infection or a disease associated with an HIV infection in a subject in need thereof, comprising administering the HTI immunogen of the invention to the subject in a priming step, followed by administering the HTI immunogen of the invention to the subject in a boosting step.

HTI Immunogens

The methods of the present invention relate to administration of HIV immunogens. International Pub. No. WO 2013/110818 and U.S. Pat. No. 9,988,425 (each of which is incorporated herein by reference in its entirety) describe immunogens for HIV vaccination (termed herein "HTI immunogens," "HTI" or "immunogenic polypeptide(s)"). Sixteen regions in the Gag, Pol, Vif, and Nef proteins of the HIV-1 virus were relatively conserved and were targeted by HIV patients having a reduced viral load of <5000 copies of HIV-1 RNA per mL Hancock et al., PLOS Pathogens 2015; 11 (2): e1004658; Mothe et al., J. Translational Med. 2015; 13:60. These regions of HIV proteins formed the basis of an immunogen for therapeutic vaccination of HIV. The following Table 1 summarizes the regions of HIV-1 targeted by the immunogens:

TABLE 1

| HIV-1 protein | Position (HXB2) | SEQ ID NO |
|---|---|---|
| p17 | 17-94 | 1 |
| p24 | 30-43 | 2 |
| p24 | 61-71 | 3 |
| p24 | 91-150 | 4 |
| p24 | 164-177 | 5 |
| p24 | 217-231 | 6 |
| p2p7p1p6 | 63-89 | 7 |
| protease | 45-99 | 8 |
| reverse transcriptase | 34-50 | 9 |
| reverse transcriptase | 210-264 | 10 |
| reverse transcriptase | 309-342 | 11 |
| integrase | 210-243 | 12 |
| integrase | 266-282 | 13 |
| Vif | 25-50 | 14 |
| Vif | 166-184 | 15 |
| Nef | 56-68 | 16 |

The HIV numbering is as described in Korber et al., Human Retroviruses and AIDS 1998. Theoretical Biology and Biophysics Group, Los Alamos National Laboratory, Los Alamos, N. Mex, pp. III-102-111 (the entire contents of which are hereby incorporated by reference).

In some embodiments, the HTI immunogen can be administered through a heterologous prime-boost vaccination that includes different components and vectors, which can be selected from viral vectors (for example, poxvirus, adenovirus, lentivirus, arenavirus and others), bacterial vectors, polypeptides, or antibodies. The aim of the sequential administration of the therapeutic vaccines is to achieve a so-called "functional cure", in which HIV-infected participants could control viral replication in the absence of anti-retroviral treatment.

In some embodiments, the methods of the present invention comprise administration of a vector (e.g., viral vector) encoding an immunogenic polypeptide (e.g., the HTI immunogen), wherein the immunogenic polypeptide comprises:

i. a sequence having at least 90%, 91%, 92%, 93%, 94%, 95%, 96%, 97%, 98%, or 99% sequence identity to SEQ ID NO:1;

ii. a sequence having at least 90%, 91%, 92%, 93%, 94%, 95%, 96%, 97%, 98%, or 99% sequence identity to SEQ ID NO:2;

iii. a sequence having at least 90%, 91%, 92%, 93%, 94%, 95%, 96%, 97%, 98%, or 99% sequence identity to SEQ ID NO:3;

iv. a sequence having at least 90%, 91%, 92%, 93%, 94%, 95%, 96%, 97%, 98%, or 99% sequence identity to SEQ ID NO:4;

v. a sequence having at least 90%, 91%, 92%, 93%, 94%, 95%, 96%, 97%, 98%, or 99% sequence identity to SEQ ID NO:5;

vi. a sequence having at least 90%, 91%, 92%, 93%, 94%, 95%, 96%, 97%, 98%, or 99% sequence identity to SEQ ID NO:6;

vii. a sequence having at least 90%, 91%, 92%, 93%, 94%, 95%, 96%, 97%, 98%, or 99% sequence identity to SEQ ID NO:7;

viii. a sequence having at least 90%, 91%, 92%, 93%, 94%, 95%, 96%, 97%, 98%, or 99% sequence identity to SEQ ID NO:8;

ix. a sequence having at least 90%, 91%, 92%, 93%, 94%, 95%, 96%, 97%, 98%, or 99% sequence identity to SEQ ID NO:9;

x. a sequence having at least 90%, 91%, 92%, 93%, 94%, 95%, 96%, 97%, 98%, or 99% sequence identity to SEQ ID NO:10;

xi. a sequence having at least 90%, 91%, 92%, 93%, 94%, 95%, 96%, 97%, 98%, or 99% sequence identity to SEQ ID NO:11;

xii. a sequence having at least 90%, 91%, 92%, 93%, 94%, 95%, 96%, 97%, 98%, or 99% sequence identity to SEQ ID NO:12;

xiii. a sequence having at least 90%, 91%, 92%, 93%, 94%, 95%, 96%, 97%, 98%, or 99% sequence identity to SEQ ID NO:13;

xiv. a sequence having at least 90%, 91%, 92%, 93%, 94%, 95%, 96%, 97%, 98%, or 99% sequence identity to SEQ ID NO:14;

xv. a sequence having at least 90%, 91%, 92%, 93%, 94%, 95%, 96%, 97%, 98%, or 99% sequence identity to SEQ ID NO:15; and xvi. a sequence having at least 90%, 91%, 92%, 93%, 94%, 95%, 96%, 97%, 98%, or 99% sequence identity to SEQ ID NO:16. In some embodiments, at least two of the sequences (i)-(xvi) are joined by a single, dual, or triple alanine amino acid linker, wherein the linker results in the formation of an AAA sequence in the junction region between adjoining sequences, and/or wherein the sequence of each of (i) to (xvi) is 11-85, e.g., from 11 to 82, from 11 to 80, or from 11 to 78, amino acids in length.

In some embodiments, the immunogenic polypeptide comprises a sequence having amino acid sequences with no more than 1, 2, or 3 substitutions in any one of SEQ ID NOs: 1-16. In some embodiments, the immunogenic polypeptide comprises a sequence having amino acid sequences according to SEQ ID NOs: 1-16.

In some embodiments, the immunogenic polypeptide comprises an amino acid sequence having at least 90%, 91%, 92%, 93%, 94%, 95%, 96%, 97%, 98%, or 99% sequence identity to SEQ ID NO:17. In some embodiments, the immunogenic polypeptide comprises an amino acid sequence according to SEQ ID NO:17.

In some embodiments, the immunogenic polypeptide is encoded by any suitable nucleic acid sequence. In some embodiments, the immunogenic polypeptide is encoded by a nucleic acid sequence having at least 90%, 91%, 92%, 93%, 94%, 95%, 96%, 97%, 98%, or 99% sequence identity to SEQ ID NO:100 or 101. In some embodiments, the immunogenic polypeptide is encoded by a nucleic acid sequence of SEQ ID NO:100 or 101. In some embodiments, the nucleic acid encodes an immunogenic polypeptide comprising SEQ ID NO:99. In some embodiments, the nucleic acid is contained in a viral vector (e.g., a MVA or ChAd vector) or a nucleic acid vector.

In other embodiments, the immunogenic polypeptide comprises SEQ ID NOs:1-16. In other embodiments, the immunogenic polypeptide comprises the sequence of SEQ ID NOs:1-16 or a variant or fragment thereof. In some embodiments, the variant has a length of at least 8 amino acids, and does not comprise any sequence stretches derived from the HIV genome of a length of 8 or more amino acids other than an amino acid sequence according to any of SEQ ID NOs:1-16 or the variant thereof. In other embodiments, the variant is equivalent to its related sequence and derives from a different HIV strain or is an artificial HIV sequence. Equivalent in this respect means different in one or more amino acid residues, but corresponding to the same sequence (e.g., determined by the position in the genome or sequence similarity). In other words, in one embodiment, the variant is a "naturally occurring variant", which refers to nucleic acid sequences derived from an HIV genome of a presently or formerly circulating virus and can be identified from existing databases (e.g., GenBank and Los Alamos sequence databases). The sequence of circulating viruses can also be determined by molecular biology methodologies. See Brown T, "Gene Cloning" (Chapman & Hall, London, G B, 1995); Watson et al., "Recombinant DNA", 2nd Ed. (Scientific American Books, New York, N.Y., US, 1992); Sambrook et al., "Molecular Cloning. A Laboratory Manual" (Cold Spring Harbor Laboratory Press, Cold Spring Harbor, N.Y., US, 1989). In some embodiments, a variant of any of SEQ ID NOs:1-16 has an amino acid sequence identity of at least 70%, at least 80%, at least 90%, at least 95%, at least 98%, or at least 99% to its corresponding sequence (i.e., SEQ ID NOs:1-16). Examples of algorithms suitable for determining percent sequence identity and sequence similarity are BLAST and BLAST 2.0 algorithms. Altschul et al., Nuc. Acids Res. 1977; 25:3389-3402 and Altschul et al., J. Mol. Biol. 1990; 215:403-410. The BLAST and BLAST 2.0 programs can be used to determine percent sequence identity for the nucleic acids and proteins of the invention. Software for performing BLAST analyses is publicly available through the National Center for Biotechnology Information. See http://blast.ncbi.nlm nih.gov/blast.cgi, January 2012.

In some embodiments, the immunogenic polypeptide comprises at least two, at least three, or at least four sequences selected from SEQ ID NOs:1-16 or variants thereof, wherein when the immunogen comprises only two, three, or four sequences selected from SEQ ID NOs:1-16, then not all of these sequences are selected from the group consisting of SEQ ID NOs:3, 5, 6 and 16. In another embodiment, said immunogen has an amino acid sequence comprising at least two, at least three, at least four, at least five, at least six, at least seven, at least eight, at least nine, or at least ten sequences selected from SEQ ID NOs:1-16 or variants thereof, wherein when the immunogen comprises only two, three, four, five, six, seven, eight, nine or ten sequences selected from the group consisting of SEQ ID NOs:1-16, then not all of these sequences are selected from the group consisting of SEQ ID NOs:1-16.

In another embodiment, the variant or fragment has a length of 8 to 40 amino acids, for example, 11 to 27 amino acids. In some embodiments, the variant or fragment does not comprise an amino acid linker adjoining any of SEQ ID NOs:1-16. In some embodiments, the C-terminal amino acid of said variant or fragment is neither G, P, E, D, Q, N, T, S, nor C.

In some embodiments, the variant or fragment is combined with or fused to a heat shock protein, for example, Hsp10, Hsp20, Hsp30, Hsp40, Hsp60, Hsp70, Hsp90, gp96, or Hsp100.

In some embodiments, the variant or fragment is selected from SEQ ID NOs:17-45.

In some embodiments, at least two sequences of the immunogenic polypeptide are adjoined by an amino acid linker. In some embodiments, the linker has the amino acid sequence A, AA or AAA. In some embodiments, if the C-terminal residue of the sequence located N-terminally with respect to the linker or the N-terminal residue of the sequence located C-terminally is an alanine residue, the linker can be shortened so that an AAA sequence is formed in the junction region between adjoining sequences. Thus, in some embodiments, if the C-terminal residue of the sequence located N-terminally with respect to the linker is an alanine or if the N-terminal residue of the sequence located C-terminally with respect to the linker is alanine, the linker has the sequence AA. In another embodiment, if the C-terminal residue of the sequence located N-terminally with respect to the linker and the N-terminal residue of the sequence located C-terminally with respect to the linker are both alanine, then the linker has the sequence A.

In another embodiment, the immunogenic polypeptide further comprises a secretion signal peptide at the N-terminus. In some embodiments, the signal peptide enhances secretion of the immunogen from cells expressing the immunogen. In some embodiments, the signal peptide is derived from GMCSF (granulocyte macrophage colony-stimulating factor), for example, followed by a valine to increase stability. The sequence of the GMCSF signal peptide is, for example, MWLQSLLLLGTVACSIS (SEQ ID NO:46) or MWLQSLLLLGTVACSISV (SEQ ID NO:47).

In another embodiment, the immunogenic polypeptide further comprises a peptide tag. In some embodiments, the peptide tag is located at the N-terminus between the signal peptide and the immunogenic polypeptide or at the C-terminus before the stop codon.

In some embodiments, the peptide tag is a FLAG peptide. The FLAG system utilizes a short, hydrophilic 8-amino acid peptide, which is fused to the recombinant protein of interest. The FLAG peptide includes the binding site for several highly specific ANTI-FLAG monoclonal antibodies (M1, M2, M5; Sigma-Aldrich Corp., Saint Louis, Mo., US), which can be used to assess expression of the protein of interest on material from transfected cells. Because of the small size of the FLAG peptide tag, it does not shield other epitopes, domains, or alter the function, secretion, or transport of the fusion protein generally. In some embodiments, the FLAG peptide has the sequence DYKDDDDKL (SEQ ID NO:48). In some embodiments, the peptide tag is only for expression analysis and/or purification of the immunogen and it is removed before using it to elicit an immune response.

In some embodiments, the sequence of the immunogenic polypeptide comprises at least one antiretroviral resistance mutation site.

Vectors

In some embodiments of the methods of the present invention, the HTI immunogen is administered via a vector. In some embodiments, the vector is an expression vector. In some embodiments, the vector is a viral vector. Examples of vectors that can be used in the present invention include, but are not limited to, prokaryotic vectors, such as pUC18, pUC19, and Bluescript plasmids and derivatives thereof, like the mp18, mp19, pBR322, pMB9, ColE1, pCR1 and RP4 plasmids; phages and shuttle vectors, such as pSA3 and pAT28 vectors; expression vectors in yeasts, such as 2-micron plasmid type vectors; integration plasmids; YEP vectors; centromeric plasmids and analogues; expression vectors in insect cells, such as the vectors of the pAC series and of the pVL series; expression vectors in plants, such as vectors of the pIBI, pEarleyGate, pAVA, pCAMBIA, pGSA, pGWB, pMDC, pMY, pORE series and analogues; and expression vectors in superior eukaryotic cells based on viral vectors (e.g., modified vaccinia Ankara (MVA), adenoviruses (e.g., chimpanzee adenovirus (ChAd)), viruses associated to adenoviruses, retroviruses and lentiviruses) as well as non-viral vectors, such as the pSilencer 4.1-CMV (Ambion®, Life Technologies Corp., Carlsbad, Calif., US), pcDNA3, pcDNA3.1/hyg pHCMV/Zeo, pCR3.1, pEF1/His, pIND/GS, pRc/HCMV2, pSV40/Zeo2, pTRACER-HCMV, pUB6N5-His, pVAX1, pZeoSV2, pCI, pSVL, pKSV-10, pBPV-1, pML2d and pTDT1 vectors.

In some embodiments, the vector comprises a promoter and polyadenylation site. In some embodiments, the vector comprises a mammalian promoter and a polyadenylation site. In some embodiments, the promoter is the human cytomegalovirus (CMV) promoter. In some embodiments, the polyadenylation site is the bovine growth hormone (BGH) polyadenylation site. Vectors of the invention can be modified to optimize vector replication in bacteria and can further comprise a selection gene, for example, a gene coding a protein conferring resistance to an antibiotic. In some embodiments, the vector comprises a kanamycin resistance gene.

In some embodiments, the vector is a viral vector, for example, a virus containing a nucleic acid that codes for the HTI immunogen of the invention. In some embodiments, the virus has low toxicity and/or is genetically stable. In some embodiments, the viral vector is a retrovirus, for example, a poxvirus such as modified vaccinia Ankara (MVA), lentivirus, adenovirus such as chimpanzee adenovirus (ChAd), arenavirus or adeno-associated virus (AAV).

Typically, an adenovirus vector useful in the invention is produced using a nucleic acid comprising the entire recombinant adenoviral genome. The adenovirus vectors useful in the invention are typically replication deficient. In these embodiments, the virus is rendered deficient by deletion or inactivation of regions critical to replication of the virus, such as the E1 region. A packaging cell line is typically used to produce sufficient amounts of adenovirus vectors for use in the invention. A packaging cell line is a cell that comprises those genes that have been deleted or inactivated in a replication deficient vector, thus allowing the virus to replicate in the cell. In some embodiments, the adenovirus is a simian adenovirus (SAds) or chimpanzee adenovirus (ChAd) (e.g., a replication deficient ChAd). Exemplary chimpanzee adenovirus vectors have been described, e.g., in U.S. Pat. No. 9,714,435 (incorporated by reference herein in its entirety).

In some embodiments, the methods of the present invention include administration of the HTI immunogen as a priming vaccine in a chimpanzee adenovirus vector (e.g., ChAdOx1.HTI). ChAdOx1 is a replication-defective recombinant chimpanzee adenovirus (ChAd) vector based on a chimpanzee adenoviral isolate Y25. ChAdOx1.HTI is a replication-defective recombinant chimpanzee adenovirus (ChAd) vector based on a chimpanzee adenoviral isolate Y25 that encodes the HTI sequence. ChAdOx1.HTI was derived by sub-cloning the HTI antigen sequence into the generic ChAdOx1 BAC in order to induce HIV-1 specific T-cell immune response. The plasmid resulting from this sub-cloning (pC255; 40,483 kbp) was linearized and transfected into commercial HEX293A T-REx® cells to produce the vectored vaccine ChAdOx1.HTI. Construction of the ChAdOx1.HTI vector was described in A. Kilpelainen et al., Vaccines (August 2019) 7(3): 78 and B. Ondondo et al., Mol. Ther. (2016) 24:832-842 (the entire contents of each of which is hereby incorporated by reference).

Booster vaccines used in the methods of the invention generally comprise one or more MVA vectors encoding an immunogenic polypeptide disclosed herein. In some embodiments, the MVA is a strain enhanced safety dueto with i) capability of reproductive replication in vitro in chicken embryo fibroblasts (CEF), but no capability of reproductive replication in a human cell line, as in the human keratinocyte cell line HaCaT, the human embryo kidney cell line 293, the human bone osteosarcoma cell line 143B, and the human cervix adenocarcinoma cell line HeLa; ii) failure to replicate in a mouse model that is incapable of producing mature B and T cells and as such is severely immune compromised and highly susceptible to a replicating virus; and iii) induction of at least the same level of specific immune response in vaccinia virus prime/vaccinia virus boost regimens when compared to DNA-prime/vaccinia virus boost regimes. In some embodiments, the MVA strain is MVA-BN. An exemplary MVA vector is described in Barouch et al. Cell; 2013, 155 (3):531-539 (herein incorporated by reference in its entirety).

In some embodiments, the methods of the present invention include administration of the HTI immunogen in a MVA vector (e.g., MVA.HTI described herein). MVA.HTI is a live, attenuated recombinant vaccinia (pox) virus attenuated by serial passages in cultured chicken embryo fibroblasts (CEF) that contains six large deletions from the parental virus genome. A transgene coding for the insert HTI has been inserted within the MVA in order to induce an HIV-1 specific T cell immune response. The size of MVA.HTI after the insertion is estimated to be approximately 7,290 kbp. The construction of the MVA.HTI vector is disclosed in U.S. Pat. Publication No. 20190055289 and in Létourneau S, Im E J, Mashishi T, Brereton C, Bridgeman A, et al. (2007) Design and Pre-Clinical Evaluation of a Universal HIV-1 Vaccine PLOS ONE 2(10): e984. Doi:10.1371/journal.pone.0000984 (the entire contents of each of which is hereby incorporated by reference).

Additional Dosing and Dosing Regimens

In some embodiments, the method of the present invention comprises (a) administering to the subject 1 to 10 (i.e., 1, 2, 3, 4, 5, 6, 7, 8, 9 or 10) administrations of a first viral vector encoding the HTI immunogen; and (b) administering to the subject 1 to 10 (i.e., 1, 2, 3, 4, 5, 6, 7, 8, 9 or 10) administrations of a second viral vector encoding the HTI immunogen. In one embodiment, the first viral vector is administered once and the second viral vector is administered once. In one embodiment, no other vectors encoding the HTI immunogen are administered in conjunction with the first and second viral vectors.

In some embodiments, the method comprises (a) administering to the subject 1 to 4 administrations of a first vector (e.g., a viral vector) encoding the HTI immunogen, and (b) administering to the subject 1 to 4 administrations of a second vector (e.g., a viral vector) encoding the HTI immunogen. In some embodiments, the method comprises (a) administering to the subject 1 to 4 administrations of a first viral vector encoding the HTI immunogen; and (b) administering to the subject 1 to 4 administrations of a second viral vector encoding the HTI immunogen.

In some embodiments, the method comprises administering to the subject 2 administrations of a first viral vector encoding the HTI immunogen. In some embodiments, the method comprises administering to the subject 3 administrations of the first viral vector encoding the HTI immunogen. In some embodiments, the method comprises administering to the subject 2 administrations of a second viral vector encoding the immunogenic polypeptide, followed by 1 administration of a first viral vector encoding the immunogenic polypeptide. In some embodiments, the method comprises administering to the subject 2 administrations of a first viral vector encoding the HTI immunogen; and administering to the subject 3 administrations of a second viral vector encoding the HTI immunogen. In some embodiments, the method comprises administering to the subject 2 administrations of an MVA vector encoding the immunogenic polypeptide; and administering to the subject 2 administrations of a ChAd vector encoding the immunogenic polypeptide, followed by 1 administration of a MVA vector encoding the immunogenic polypeptide. In some embodiments of such a method, the administrations of the first viral vector (e.g., ChAdOx1.HTI) are at a dose of about $1 \times 10^8$ to about $1 \times 10^{11}$ viral particles (vp). In a particular embodiment, the first viral vector is ChAdOx1.HTI and is administered at a dose of about $5 \times 10^{10}$ vp. In some embodiments, the second viral vector (e.g., MVA.HTI) is administered at a dose of about $1 \times 10^6$ to about $1 \times 10^{10}$ plaque forming units (pfu). In a particular embodiment, the second viral vector is MVA.HTI and is administered at a dose of about $2 \times 10^8$ pfu. In one embodiment of the method of the invention, the first viral vector is ChAdOx1.HTI and is administered to a subject in need thereof at a dose of about $5 \times 10^{10}$ vp and the second viral vector is MVA.HTI and is administered to the subject at a dose of about $2 \times 10^8$ pfu about 8 weeks after the first viral vector is administered. In some embodiments, the first viral vector is an MVA vector as immediately above. In some embodiments, the second viral vector is a ChAd vector.

In other embodiments, the method comprises (a) administering to the subject 2 administrations of a first viral vector encoding the immunogenic polypeptide, each separated by a period of about 12 weeks; and (b) administering to the subject 2 administrations of a second viral vector encoding the immunogenic polypeptide, each separated by a period of about 12 weeks; and wherein the administering of (b) is separated from the administering of (a) by a period of about 12 weeks. In some embodiments, the administrations of (a) are at a dose of about $5 \times 10^{10}$ viral particles, and/or the administrations of (b) are at a dose of about $2 \times 10^8$ pfu. In some embodiments, the first viral vector is a ChAd vector. In some embodiments, the second viral vector is an MVA vector.

Immunogenic polypeptides and polynucleotides and vectors encoding the same of the invention can be administered in a variety of routes, for example, via the mucosa, such as oral and nasal, pulmonary, intramuscular, subcutaneous or intradermal routes.

Immunogenic polypeptides and polynucleotides and vectors encoding the same of the invention can also be administered in a pharmaceutical composition comprising a pharmaceutically acceptable carrier (also referred to herein as a vaccine or vaccine formulation). Examples of a pharmaceutically acceptable carrier include, but are not limited to, a solid, semisolid or liquid filler, diluent, encapsulating material or formulation auxiliary of any conventional type. Other suitable pharmaceutically acceptable carriers include, but are not limited to, water, dextrose, glycerol, saline, ethanol, and combinations thereof. In some embodiments, a pharmaceutically acceptable carrier can contain additional agents such as wetting or emulsifying agents, pH buffering agents, or adjuvants that enhance the effectiveness of the formulation.

In addition, aqueous compositions, such as those used to prepare HIV vaccine formulations, may be prepared in sterile form, and when intended for delivery by other than oral administration generally may be isotonic. All compositions may optionally contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like.

In some embodiments, a pharmaceutical composition comprises 0.5 mL Tris buffer (10 mM Tris HCl, pH 7.7, 140 mM NaCl). In some embodiments, the pharmaceutical composition comprises $2 \times 10^8$ plaque forming units (PFU) of a viral vector encoding the HTI immunogen in 0.5 mL Tris buffer (10 mM Tris HCl, pH 7.7, 140 mM NaCl). In some embodiments, the pharmaceutical composition comprises $2 \times 10^8$ plaque forming units (PFU) of an MVA vector encoding the HTI immunogen in 0.5 mL Tris buffer (10 mM Tris HCl, pH 7.7, 140 mM NaCl). In some embodiments, the pharmaceutical composition comprises $2 \times 10^8$ plaque forming units (PFU) of an MVA vector comprising a nucleic acid encoding an immunogenic polypeptide having an amino acid sequence of SEQ ID NO:99 in 0.5 mL Tris buffer (10 mM Tris HCl, pH 7.7, 140 mM NaCl). In some embodiments, the pharmaceutical composition comprises $2 \times 10^8$ PFU of an MVA vector comprising a nucleic acid comprising the sequence of SEQ ID NO:100 or 101 in 0.5 mL Tris buffer (10 mM Tris HCl, pH 7.7, 140 mM NaCl).

In some embodiments, a pharmaceutical composition of the invention comprises a viral vector, e.g., ChAdOx1.HTI and L-Histidine: 10 mM NaCl: 35 mM; Sucrose: 7.5% (w/v); MgCl2: 1 mM; EDTA disodium: 0.1 mM; Tween 80 (Polysorbate-80): 0.1% (w/v); Ethanol 0.5%: (v/v); HCl: Adjusted to pH 6.6. In a particular embodiment, the pharmaceutical composition comprises $5 \times 10^{10}$ vp of ChAdOx1.HTI and L-Histidine: 10 mM NaCl: 35 mM; Sucrose: 7.5% (w/v); MgCl2: 1 mM; EDTA disodium: 0.1 mM; Tween 80 (Polysorbate-80): 0.1% (w/v); Ethanol 0.5%: (v/v); HCl: Adjusted to pH 6.6.

It should be understood that description herein related to the administration of an immunogenic polypeptide or nucleic acid encoding an immunogenic polypeptide also applies to administration of a pharmaceutical composition or vaccine containing the same.

The amount of the virus within a pharmaceutical composition can be measured by any means known in the art. The amount may be determined by bulk measurement of the number of viral particles (vp) within an amount of aqueous composition, e.g., by flow cytometry. Alternatively, the amount may be determined by the activity of the virus within the composition, e.g., by plaque assay. Plaque-based assays can be used to determine virus concentration in terms of infectious dose. Viral plaque assays determine the number of plaque forming units (pfu) in a virus sample, which can be used as a measure of virus quantity. Kaufmann et al. 2002; Methods in Microbiology Vol. 32: Immunology of Infection. Academic Press. ISBN 0-12-521532-0.

In some embodiments, a viral vector (e.g., MVA or ChAd vector) encoding an immunogenic polypeptide of the present invention is administered at a dose of from about $1 \times 10^7$ plaque forming units (pfu) to about $1 \times 10^9$ pfu, for example, from about $5 \times 10^7$ pfu to about $1 \times 10^9$ pfu, from about $1 \times 10^8$ pfu to about $1 \times 10^9$ pfu, from about $5 \times 10^8$ pfu to about $1 \times 10^9$ pfu. In some embodiments, a viral vector encoding an immunogenic polypeptide of the present invention is administered at a dose of from about $5 \times 10^7$ pfu to about $5 \times 10^8$ pfu. In some embodiments, a viral vector encoding an immunogenic polypeptide of the present invention is administered at a dose of about $2.5 \times 10^8$ pfu. In some embodiments, a viral vector encoding an immunogenic polypeptide of the present invention is administered at a dose of about $1 \times 10^7$ pfu, about $1 \times 10^8$ pfu, about $1 \times 10^9$ pfu, about $5 \times 10^7$ pfu or about $5 \times 10^8$ pfu.

In some embodiments, a viral vector (e.g., MVA or ChAd vector) encoding an immunogenic polypeptide of the present invention is administered at a dose of from about $1 \times 10^9$ viral particles (vp) and $5 \times 10^{11}$ viral particles, for example, from about $5 \times 10^9$ vp to about $5 \times 10^{11}$ vp, from about $1 \times 10^{10}$ vp to about $5 \times 10^{11}$ vp, from about $5 \times 10^{10}$ vp to about $5 \times 10^{11}$ vp, or from about $1 \times 10^{11}$ vp to about $5 \times 10^{11}$ vp. In some embodiments, a viral vector encoding an immunogenic polypeptide of the present invention is administered at a dose of from about $1 \times 10^{10}$ to about $1 \times 10^{11}$ viral particles, for example, from about $5 \times 10^{10}$ vp to about $1 \times 10^{11}$ vp. In some embodiments, a viral vector encoding an immunogenic polypeptide of the present invention is administered at a dose of from about $5 \times 10^{10}$ viral particles.

The amount of immunogenic compound (e.g., HTI immunogen) delivered can vary, depending upon the intended use (preventive or therapeutic vaccination), and age and weight of the subject to be immunized, the vaccination protocol adopted (i.e., single administration versus repeated doses), the route of administration and the potency and dose of the adjuvant compound chosen. The amount can be ascertained by standard studies involving observation of appropriate immune responses in vaccinated subjects. In some embodiments, following an initial vaccination, composed itself by one or several doses, subjects can receive one or several booster immunization adequately spaced.

In some embodiments, an immunogenic compound or composition is administered on an one-off basis, or can be administered repeatedly, for example, from about 1 and about 10 times, for example, from about 1 to about 9 times, from about 1 to about 8 times, from about 1 to about 7 times, from about 1 to about 6 times, from about 1 to about 5 times, from about 1 to about 4 times, from about 1 to about 3 times, from about 1 to about 2 times, from about 2 to about 9 times, from about 2 to about 8 times, from about 2 to about 7 times, from about 2 to about 6 times, from about 2 to about 5 times, from about 2 to about 4 times, from about 2 to about 3 times, from about 3 to about 9 times, from about 3 to about 8 times, from about 3 to about 7 times, from about 3 to about 6 times, from about 3 to about 5 times, from about 3 to about 4 times, from about 4 to about 9 times, from about 4 to about 8 times, from about 4 to about 7 times, from about 4 to about 6 times, or from about 4 to about 5 times.

In some embodiments, an immunogenic compound or composition is administered at different intervals between doses of the same component or doses of different component. In some embodiments, the interval between doses is from about 1 week to about 24 months, for example, from about 2 weeks to about 24 months, from about 3 weeks to about 24 months, from about 4 weeks to about 24 months, from about 2 weeks to about 56 weeks, from about 4 weeks and about 12 weeks.

In other embodiments, each administration of the methods of the present invention is separated by a period of from about 15 days to about 18 months. In some embodiments, each administration of the methods of the present invention is separated by a period of from about 1 week to about 24 months. In some embodiments, each administration of the methods of the present invention is separated by a period of from about 2 weeks to about 56 weeks. In some embodiments, each administration of the methods of the present invention is separated by a period of from about 4 weeks to about 12 weeks. In some embodiments of the methods of the present invention, the administering of step (a) of the methods of the present invention is separated from the administering of step (b) by a period of from about 2 months to about 24 months. In some embodiments of the methods of the present invention, the administering of step (a) is separated from the administering of step (b) by a period of from about 3 months to about 18 months.

In some embodiments, the vaccine components of the present invention can be grouped in a priming phase and a subsequent one or multiple boosting phases. In some embodiments, the priming phase and the boosting phase can be separated by from about 2 weeks to about 24 weeks, for example, from about 3 weeks to about 18 weeks. In some embodiments, the subject will receive the immunogen compound or composition of the invention as different vaccine components in a prime-boost regime. In one embodiment, the subject in need of treatment is administered ChAdOx1.HTI in a priming phase and is then administered MVA.HTI in a boosting phase. The time period between the priming administration and the boosting administration can be, for example, 8 weeks. In some embodiments, such a regimen is followed by dosing at regular intervals of from about 1 months to about 12 months for a period up to the remainder of the subject's life.

In one particular embodiment, the ChAdOx1.HTI vector (C) is administered as a priming dose and the MVA.HTI vector (M) is then administered as a boosting dose. In one embodiment, C and M are each administered in a single administration. In another embodiment, one or both of C and M are administered in multiple administrations. In a particular embodiment, C is administered on day zero (DO) at a dose of $5 \times 10^{10}$ Vp and M is administered on day 56 (D56) at a dose of $2 \times 10^8$ pfu. For each administration, the dose can be administered intramuscularly and the volume can be 500 ul.

In some embodiments, the immunogenic compounds or compositions of the invention are used in any sequence, each component can be used one or several times, in any order, and with any interval between doses.

In some embodiments, the sequence comprises a priming phase of CC ($5 \times 10^{10}$ viral particles each), at week 0 and week 12, followed by a boosting phase of a first dose of M 12 weeks after the last C and a second dose of M 12 weeks after the first M (each dose of M of $2 \times 10^8$ pfu).

HIV Infection or a Disease Associated with an HIV Infection and Other Methods In some embodiments, the present invention is directed to a method of treating or preventing HIV infection or a disease associated with an HIV infection. In some embodiments, the HIV is HIV type 1 (HIV-1). In some embodiments, the HIV is HIV type 2 (HIV-2).

In some embodiments, the disease associated with an HIV infection is an acquired immune deficiency syndrome (AIDS), AIDS-related complex (ARC), or HIV opportunistic disease. In some embodiments, the HIV opportunistic disease is Burkitt's lymphoma, candidiasis in the bronchi, trachea, lungs, or esophagus, cervical cancer, coccidioidomycosis (disseminated or outside the lungs), cryptococcosis (outside the lungs), cryptosporidiosis (in the intestines lasting for more than 1 month), cytomegalovirus infection (outside the liver, spleen, or lymph nodes), cytomegalovirus retinitis (with loss of vision), HIV encephalopathy, herpes simplex lesions lasting for more than one month, herpes simplex in the bronchi, lung, or esophagus, histoplasmosis (disseminated or outside the lungs), immunoblastic lymphoma, invasive cervical carcinoma (cancer), isosporiasis in the intestines lasting for more than one month, Kaposi's sarcoma, lymphoma (primary in the brain), *Mycobacterium avium* complex (disseminated or outside the lungs), *Mycobacterium kansasii* (disseminated or outside the lungs), *Mycobacterium tuberculosis* (disseminated or outside the lungs), *Pneumocystis carinii* pneumonia, pneumonia (recurrent in 12 month period), progressive multifocal leukoencephalopathy (PML), salmonella septicemia (recurrent), toxoplasmosis (in the brain), wasting syndrome or any other disease resulting from an infection facilitated by a compromised immune system in an HIV-infected patient.

In some embodiments of the methods of the present invention, one or more of the following clinical effects are observed in non-HIV-infected subjects: avoiding the HIV infection in at least 30% of vaccinated individuals, or more desirably avoiding the HIV infection in more than 50% of vaccinated individuals. In some embodiments, the HIV is HIV-1.

In some embodiments of the methods of the present invention, one or more of the following clinical effects are observed in HIV-infected subjects: (1) a substantial reduction of the HIV-1 viral load in the subject's blood and tissues for a significant amount of time (non-progressor phenotype), typically under 2,000 copies of viral RNA per ml of plasma, or more desirably, under 50 copies of viral RNA per ml of plasma (2) a reduction or remission in AIDS-related clinical symptoms, and (3) a reduction in the conventional antiretroviral treatment, more desirably the complete interruption of the cART. A reduction or remission of AIDS-related clinical symptoms includes, but is not limited to, prolonging the asymptomatic phase of HIV infection; maintaining low viral loads in HIV infected patients whose virus levels have been lowered via anti-retroviral therapy (ART); increasing levels of CD4 T cells or lessening the decrease in CD4 T cells, both HIV-1 specific and non-specific, in drug naive patients and in patients treated with ART, increasing the breadth, magnitude, avidity and functionality of HIV specific CTL, increasing overall health or quality of life in an individual with AIDS; and prolonging life expectancy of an individual with AIDS. A clinician can compare the effect of immunization with the patient's condition prior to treatment, or with the expected condition of an untreated patient, to determine whether the treatment is effective in inhibiting AIDS.

In some embodiments, the methods of the present invention relate to generating a T-cell cellular response in a subject by administration of an immunogenic polypeptide described herein using a dosing regimen described herein.

In some embodiments, the methods of the present invention generate an effective cytotoxic T cell response. A cytotoxic T cell or cytotoxic T lymphocyte (CTL) assay can be used to monitor the cellular immune response following subgenomic immunization with a viral sequence against homologous and heterologous HIV strains. Burke et al., J. Inf. Dis. 1994; 170:1110-1119 and Tigges et al., J. Immunol, 1996; 156:3901-3910. Conventional assays utilized to detect T cell responses include, for instance, proliferation assays, lymphokine secretion assays, direct cytotoxicity assays and limiting dilution assays. For example, antigen-presenting cells that have been incubated with a peptide can be assayed for their ability to induce CTL responses in responder cell populations. Antigen-presenting cells can be cells such as peripheral blood mononuclear cells (PBMCs) or dendritic cells (DCs). Alternatively, mutant non-human mammalian cell lines that are deficient in their ability to load MHC class I molecules with internally processed peptides and that have been transfected with the appropriate human MHC class I gene, can be used to test the capacity of a peptide of interest to induce in vitro primary CTL responses. PBMCs can be used as the responder cell source of CTL precursors. The appropriate antigen-presenting cells are incubated with the peptide after which the protein-loaded antigen-presenting cells are incubated with the responder cell population under optimized culture conditions. Positive CTL activation can be determined by assaying the culture for the presence of CTL that kill radiolabeled target cells, both specific peptide-pulsed targets as well as target cells expressing endogenously processed forms of the antigen from which the peptide sequence was derived. For example, the target cells can be radiolabeled with $^{51}$Cr and cytotoxic activity can be calculated from radioactivity released from the target cells. Another suitable method allows the direct quantification of antigen-specific T cells by staining with fluorescein-labeled HLA tetrameric complexes. Altman et al., Proc. Natl. Acad. Sci. USA 1993; 90:10330-10334 and Altman et al., Science 1996; 274:94-96. Other relatively recent technical developments include staining for intracellular lymphokines and interferon release assays or ELISpot assays.

In some embodiments of the methods of the present invention, the subject is a human subject.

Combination Therapies

In some embodiments, the methods of the invention comprise administering the first and second viral vectors encoding the immunogenic polypeptidein conjunction with one or more other anti-HIV therapies, including but not limited to anti-retroviral therapy (ART). In the case of preventive vaccination, the subject receiving the therapy of the invention will normally not have been taking ART. However, in the case of therapeutic vaccination, the subject will in many cases have been taking ART. The methods of the invention can also be used in conjunction with Pre-Exposure Prophylaxis (PrEP) techniques. Other anti-HIV therapies can be administered concurrently or sequentially with the first and second viral vectors of the invention. In some embodiments, the anti-retroviral therapy comprises an HIV reverse transcriptase inhibitor (e.g., a nucleoside or non-nucleoside reverse transcriptase inhibitor), an HIV integrase inhibitor, an HIV non-catalytic site (or allosteric) integrase inhibitor, an HIV entry (fusion) inhibitor, an HIV maturation inhibitor, or a combination thereof. Exemplary anti-retroviral agents include the HIV integrase catalytic site inhibitors raltegravir (ISENTRESS®; Merck), bictegravir (Gilead), elvitegravir (Gilead), soltegravir (GSK, ViiV), cabotegravir (GSK 1265744, GSK744, GSK, ViiV), and dolutegravir; HIV nucleoside reverse transcriptase inhibitors abacavir (ZIAGEN®, GSK), didanosine (VIDEX®, BMS), tenofovir disoproxil fumarate (VIREAD®, Gilead), tenofovir alafenamide (TAF), emtricitabine (EMTRIVA®, Gilead), lamivudine (EPIVIR®, GSK/Shire), stavudine (ZERIT®, BMS), zidovudine (RETROVIR®, GSK), abacavir, elvucitabine (Achillion), tenofovir exalidex (CMX-157, Chimerix), and festinavir (Oncolys); HIV non-nucleoside reverse transcriptase inhibitors nevirapine (VIRAMUNE®, BI), efavirenz (SUSTIVA®, BMS), etravirine (INTELENCE®, J&J), rilpivirine (TMC278, R278474, J&J), fosdevirine (GSK, ViiV), doravirine (MK-1439, Merck), and lersivirine (Pfizer/ViiV); HIV protease inhibitors atazanavir (REYATAZ®, BMS), darunavir (PREZISTA®, J&J), indinavir (CRIXIVAN®, Merck), lopinavir (KALETRA®, Abbvie), nelfinavir (VIRACEPT®, Pfizer), saquinavir (INVIRASE®, Hoffmann-LaRoche), tipranavir (APTIVUS®, BI), ritonavir (NORVIR®, Abbvie), and fosamprenavir (LEXIVA®, GSK/Vertex); HIV entry inhibitors maraviroc (SELZENTRY®, Pfizer), enfuvirtide (FUZEON®, Trimeris), and fostemsavir (BMS-663068, BMS); and the HIV maturation inhibitor bevirimat (Myriad Genetics).

In some embodiments, the anti-retroviral therapy comprises one or more agents selected from the group consisting of raltegravir, elvitegravir, soltegravir, cabotegravir, dolutegravir, abacavir, didanosine, tenofovir disoproxil fumarate, tenofovir alafenamide, emtricitabine, lamivudine, stavudine, zidovudine, abacavir, elvucitabine, tenofovir exalidex, festinavir, nevirapine, efavirenz, etravirine, rilpivirine, fosdevirine, doravirine, lersivirine, atazanavir, darunavir, indinavir, lopinavir, nelfinavir, saquinavir, tipranavir, ritonavir, fosamprenavir, maraviroc, enfuvirtide, fostemsavir, bevirimat, cobicistat, and bictegravir; or a pharmaceutically acceptable salt thereof. In some embodiments, the anti-retroviral therapy comprises one or more agents selected from the group consisting of raltegravir, soltegravir, cabotegravir, dolutegravir, abacavir, didanosine, tenofovir disoproxil fumarate, tenofovir alafenamide, emtricitabine, lamivudine, stavudine, zidovudine, abacavir, elvucitabine, tenofovir exalidex, festinavir, rilpivirine, fosdevirine, doravirine, lersivirine, maraviroc, enfuvirtide, fostemsavir, bevirimat, and bictegravir; or a pharmaceutically acceptable salt thereof. In some embodiments, the anti-retroviral therapy comprises three or more agents, e.g., two nucleoside reverse transcriptase inhibitors and a non-nucleoside reverse transcriptase inhibitor or an integrase inhibitor In some embodiments, the method of treating or preventing an HIV infection comprises administration of a TLR7 modulating compound and an HIV vaccine of the invention. Such administration can be after administration of ART. In some embodiments, the method of treating or preventing an HIV infection comprises administration of a TLR7 modulating compound and an HIV vaccine concurrently with ART. In some embodiments, the therapeutic agents of the ART is the same before and during administration of the TLR7 modulating compound and the HIV vaccine. In some embodiments, the therapeutic agents of the ART is different before and during administration of the TLR7 modulating compound and the HIV vaccine.

Kits

In some embodiments, the present invention relates to a kit comprising immunogenic polypeptide of the invention, or one or more viral vectors encoding the same, or a pharmaceutical composition comprising the same, and instructions for using the same in a method of present invention described herein. In some embodiments, the kit comprises a packaging, such as glass, plastic (e.g., polyethylene, polypropylene, polycarbonate), bottles, vials, paper, or sachets for the components. In some embodiments, the instructions are in the form of printed material or in the form of an electronic support which can store the instructions, for example, electronic storage media (e.g., magnetic disks, tapes), or optical media (e.g., CD-ROM, DVD). The media can additionally or alternatively contain internet websites providing such instructions.

All publications, patents and patent applications mentioned in this application are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Embodiments of the present disclosure can be further defined by reference to the following non-limiting examples, which describe in detail preparation of some antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

Construction of the ChAdOx1.HTI Vaccine

ChAdOx1.HTI is a replication-defective recombinant chimpanzee adenovirus (ChAd) vector based on a chimpanzee adenoviral isolate Y2546 that encodes the HTI sequence. ChAdOx1.HTI was derived by sub-cloning the HTI antigen sequence into the generic ChAdOx1 BAC (Oxford University). The plasmid resulting from this sub-cloning (pC255; 40,483 kbp) was linearized and transfected into commercial HEX293A T-REx® cells to produce the vectored vaccine ChAdOx1.HTI. ChAdOx1.HTI was formulated as a suspension for intramuscular (i.m.) injection. The buffer for injection contained 10 mM of L-Histidine, 35 mM of NaCl, 7.5% (w/v) of sucrose, 1 mM of $MgCl_2$, 0.1 mM of EDTA disodium, 0.1% (w/v) of Polysorbate-80, and 0.5% (v/v) of ethanol. pH was adjusted with HCl to 6.6. Vials were stored at −80° C.

Example 2

Construction of MVA.HTI

MVA.HTI was constructed as described in US Patent Publication No. 2019/0055289 (the entire contents of which is hereby incorporated by reference).

Example 3

Clinical Efficacy of the C Priming Followed by the M Boosting in Non HIV-Infected Volunteers The C priming followed by M boosting is tested in non HIV-infected volunteers in a safety and immunogenicity trial entitled: A phase 1/2a open label trial to assess safety and immunogenicity of candidate T-cell vaccines ChAdOx1.HTI and MVA.HTI given sequentially to healthy HIV-1/2 negative adult volunteers.

Briefly, 10 HIV-1/2 negative, low-risk males and females 18-65 years of age are recruited to assess the safety profile and the immunogenicity of vaccines ChAdOx1.HTI and MVA.HTI administered sequentially.

The study design includes thirteen visits over 8 months; screening, D0 (ChadOx1.HTI vaccination), D1, D7, D14, D28, D56 (MVA.HTI vaccination), D57, D63, D70, D84, D140, D224. (D=day).

The compositions tested are:

| Vaccine | Dosage | Formulation | Volume Injected (approximate) |
|---|---|---|---|
| MVA.HTI (M) | $2 \times 10^8$ pfu | Tris pH 7.7 | 500 µl i.m. |
| ChAdOx1.HTI (C) | $5 \times 10^{10}$ Vp | L- Histidine: 10 mM NaCl: 35 mM Sucrose: 7.5% (w/v) MgCl2: 1 mM; EDTA disodium: 0.1 mM Tween 80 (Polysorbate-80): 0.1% (w/v) Ethanol 0.5%: (v/v) HCl: Adjusted to pH 6.6 | 500 µl i.m. |

The Primary Objective of the study is to confirm the safety of the ChAdOx1.HTI and MVA.HTI vaccines administered sequentially by intramuscular needle injection in heterologous prime-boost regimen into healthy, HIV-1/2-negative adult volunteers. The Primary Outcome Measures are: (1) The specific endpoints for safety and reactogenicity are actively and passively collected data on adverse events, (2) The following parameters are assessed: Occurrence of solicited local reactogenicity signs and symptoms for 7 days following vaccination; Occurrence of solicited systemic reactogenicity signs and symptoms for 7 days following vaccination; Occurrence of unsolicited adverse events for 28 days following vaccination; Change from baseline for safety laboratory measures; Occurrence of serious adverse events during the whole study duration.

The Secondary Objective of the study is to confirm the immunogenicity of the ChAdOx1.HTI and MVA.HTI vaccines administered sequentially by intramuscular needle injection in heterologous prime-boost regimen into healthy, low-risk, HIV-1-uninfected adult volunteers. The Secondary Outcome Measures are: (1) Proportion of patients that develop T cell responses to HTI-encoded regions as determined by IFN-γ ELISPOT assay; (2) Breadth of total vaccine induced HIV-1-specific responses measured IFN-γ ELISPOT in vaccine recipients; (3) Magnitude of total vaccine induced HIV-1-specific responses measured IFN-γ ELISPOT This study is conducted in healthy adults, who meet the following inclusion and exclusion criteria:

Inclusion Criteria are, among others:
Healthy adults aged 18-65 years
Able and willing (in the Investigator's opinion) to comply with all study requirements
Willing to allow the investigators to discuss the volunteer's medical history with their General Practitioner
Agreement to refrain from blood donation during the course of the study
In the opinion of the Investigators, the volunteer has understood the information provided. Written informed consent must be given before any study-related procedures are performed
Willing to undergo HCV, HBV, syphilis and HIV testing, counselling and receive test results.
Exclusion Criteria are, among others:
Confirmed HIV-1 or HIV-2 infection
Participation in another research study involving receipt of an investigational product in the 30 days preceding enrolment, or planned use during the study period
Prior receipt of a recombinant simian adenoviral vaccine
Receipt of any investigational HIV-1 vaccine within the last 6 years
Receipt of live attenuated vaccine within the previous 60 days or planned receipt within 60 days after vaccination with the IMP Receipt of other vaccine, including influenza vaccine, within the previous 14 days or planned receipt within 14 days after vaccination with the IMP Administration of immunoglobulins and/or any blood products within the three months preceding the planned administration of the vaccine candidate Any confirmed or suspected immunosuppressive or immunodeficient state, including HIV-1 infection; asplenia; recurrent, severe infections and chronic (more than 14 days) immunosuppressant medication within the past 6 months (inhaled and topical steroids are allowed).

Administration of the vectors demonstrates that they are safe and effective at inducing an immune response in the subject.

Example 4

Clinical Efficacy of the C Priming Followed by M Boosting in HIV-1 Positive Individuals The C priming sequence, followed by M boosting is tested in HIV positive individuals, in a safety and immunogenicity trial entitled: Phase I Randomized, Double-Blind, Placebo-Controlled Safety, Tolerability and Immunogenicity Study of Candidate HIV-1 Vaccines ChAdOx1.HTI and MVA.HTI and in cART Treated HIV-1 Positive Individuals. Briefly, 30 individuals are recruited to confirm safety, immunogenicity and efficacy of two vaccines administered in a heterologous prime-boost regimen CM, followed by an ATI period to monitor for viral rebound kinetics. The 30 healthy, well-controlled ART treated, HIV-1 positive males and females, 18-60 years of age are randomized 2:1 to the CM and Placebo groups.

The design of the Study is as follows:
Group 1. CM:
  ChAdOx1.HTI at Week 0 (1 dose of $5\times10^{10}$ vp)
  MVA.HTI at Week 8 (1 dose of $2\times10^{8}$ pfu)
Group 2. Placebo:
  Normal saline buffer at Week 0 and Week 8
  (ATI=Analytical Treatment Interruption; EOS=End Of Study)
Compositions tested are:

| Vaccine | Dosage | Formulation | Volume Injected (approximate) |
|---|---|---|---|
| MVA.HTI (M) | $2 \times 10^8$ pfu | Tris pH 7.7 | 500 µl i.m. |
| ChAdOx1.HTI (C) | $5 \times 10^{10}$ Vp | L-Histidine: 10 mM NaCl: 35 mM Sucrose: 7.5% (w/v) MgCl2: 1 mM; EDTA disodium: 0.1 mM Tween 80 (Polysorbate-80): 0.1% (w/v) Ethanol 0.5%: (v/v) HCl: Adjusted to pH 6.6 | 500 µl i.m. |
| Placebo | | Normal Saline buffer 0.9% NaCl | 500 µl |

The Primary Objective is to evaluate the safety and immunogenicity of a heterologous prime-boost regimen with ChAdOx1.HTI and MVA.HTI in immune competent, cART treated HIV-1 positive individuals. The Primary Endpoints are the proportion of participants that develop Grade 3 or 4 local reactions; the proportion of participants that develop Grade 3 or 4 systemic reactions, and a descriptive summary of any local and systemic events, including laboratory abnormalities, including severity, durability and relationship to study product in vaccine and placebo recipients.

The Secondary Objectives are (1) to evaluate the immunogenicity of ChAdOx1.HTI and MVA.HTI vaccines as part of heterologous prime-boost regimens (CM) in ART-treated HIV-1 positive individuals with robust immune system and (2) to evaluate whether the heterologous prime-boost vaccination of ChAdOx1.HTI and MVA.HTI vaccines is able to prevent or delay viral rebound, induce post-rebound viral control, and/or prevent or delay the need for resumption of antiretroviral therapy during an analytical treatment interruption (ATI) of antiretroviral therapy in ART treated HIV-1 positive individuals with robust immune system. The Secondary Endpoints are: (1) T-cell Immunogenicity: Proportion of participants that develop de-novo T cell responses to HTI-encoded regions as determined by IFN-γ ELISPOT assay in vaccine and placebo recipients; Breadth and magnitude of total HTI-specific and total HIV-specific T cell responses measured by IFN☐ ELISPOT in vaccine and placebo recipients; (2) Viral rebound during an ATI period: Percentage of participants with sustained viral remission, defined as plasma viral load (pVL)<50 copies/mL at 12 weeks after ATI start (visit week 16); Time to viral detection, defined as the time from ATI start (visit week 16) to first occurrence of detectable pVL (>50 copies/mL); Time to viral rebound, defined as the time from ATI start (visit week 16) to first occurrence of pVL>10,000 copies/mL; Percentage of participants who remain off cART at 12 weeks after ATI (visit week 28); Time off cART, defined as time to cART resumption since ATI start (visit week 16); (3) Safety of an analytic ART interruption period (from week 16 to week 28): Proportion of participants who develop symptoms compatible with acute retroviral syndrome (ARS); Proportion of participants who develop new mutations not present in the pre-cART viral genotype conferring clinically-significant resistance to antiretroviral drugs (out of the individuals not reaching viral re-suppression 12 weeks after cART resumption); During the post-ATI cART resumption safety follow-up period of 12 weeks (from week 28 to week 40): Proportion of participants who suppress pVL to <50 copies/mL 12 weeks after cART resumption. In those participants not reaching viral re-suppression 12 weeks after cART resumption an ART viral genotype is analysed from the ATI sample to address if new drug-resistance mutations have emerged.

Inclusion Criteria are, among others:
  Males and females aged 18-60 years
  Confirmed HIV-1 infection
  On combined antiretroviral treatment (defined as ≥3 antiretroviral drugs)
  Willing and able to be adherent to their cART regimen for the duration of the study.
  Optimal virological suppression for at least 3 years defined as maintained pVL below the limit of detection (based on current available assays, 20, 40 or 50 copies/ml) allowing for isolated blips (<200 cop/ml, non-consecutive, representing <10% total determinations).
  Being on the same cART regimen for at least 4 weeks at screening visit.
  Nadir CD4 count≥500 cells per mm3.
  Aged at least 18 years on the day of screening and no greater than 60 years on the day of the first IMP administration.
  Willing to comply with the requirements of the protocol and available for follow-up for the planned duration of the study.

In the opinion of the principal investigator or designee, the participant has understood the information provided and capable of giving written informed consent.

Exclusion Criteria are among others:

Pregnancy or lactating.

When available, pre-cART genotypic data that demonstrates the presence of clinically significant drug resistance mutations that would prevent the construction of a viable cART regimen post-treatment interruption Reported periods of suboptimal adherence to cART History of past antiretroviral treatment interruptions longer than 2 weeks.

Participation in another clinical trial that involves a treatment intervention (active arm) within 12 weeks of study entry (at screening visit).

Any AIDS-defining disease or progression of HIV-related disease.

History of autoimmune disease.

History or clinical manifestations of any physical or psychiatric disorder which could impair the subject's ability to complete the study.

Receipt of approved vaccines within 2 weeks of study entry and along the duration of the trial 1

History of anaphylaxis or severe adverse reaction to vaccines.

Previous immunisation with any experimental immunogens.

Receipt of blood products within 6 months of study entry.

Treatment for cancer or lymphoproliferative disease within 1 year of study entry.

Any other current or prior therapy which, in the opinion of the investigators, would make the individual unsuitable for the study or influence the results of the study.

Current or recent use (within last 3 months) of interferon or systemic corticosteroids or other immunosuppressive agents (use on inhaled steroids for asthma or topic steroids for localized skin conditions are permitted).

Administration of ChAdOx1.HTI vaccine and the MVA.HTI vaccine induces an immune response against a human immunodeficiency virus (HIV), e.g., HIV-1 or HIV-2, in the subjects. In some subjects, the immune response is sufficient to treat or prevent a human immunodeficiency virus (HIV) infection or a disease associated with an HIV infection. In some subjects virologic suppression is achieved. In other subjects, virologic suppression is maintained.

What is claimed is:

1. A method for inducing an immune response against a human immunodeficiency virus (HIV) in a subject in need thereof comprising a prime-boost regimen of:
   (a) administering to the subject 1 to 10 administrations of an immunogenically effective amount of a first viral vector encoding an immunogenic polypeptide as a prime, followed by;
   (b) administering to the subject 1 to 10 administrations of an immunogenically effective amount of a second viral vector encoding the immunogenic polypeptide as a boost;
   wherein said immunogenic polypeptide comprises:
   (i) a sequence having at least 95% identity to the sequence of SEQ ID NO:1,
   (ii) a sequence having at least 95% identity to the sequence of SEQ ID NO:2,
   (iii) a sequence having at least 95% identity to the sequence of SEQ ID NO:3,
   (iv) a sequence having at least 95% identity to the sequence of SEQ ID NO:4,
   (v) a sequence having at least 95% identity to the sequence of SEQ ID NO:5,
   (vi) a sequence having at least 95% identity to the sequence of SEQ ID NO:6,
   (vii) a sequence having at least 95% identity to the sequence of SEQ ID NO:7,
   (viii) a sequence having at least 95% identity to the sequence of SEQ ID NO:8,
   (ix) a sequence having at least 95% identity to the sequence of SEQ ID NO:9,
   (x) a sequence having at least 95% identity to the sequence of SEQ ID NO:10,
   (xi) a sequence having at least 95% identity to the sequence of SEQ ID NO:11,
   (xii) a sequence having at least 95% identity to the sequence of SEQ ID NO:12,
   (xiii) a sequence having at least 95% identity to the sequence of SEQ ID NO:13,
   (xiv) a sequence having at least 95% identity to the sequence of SEQ ID NO:14,
   (xv) a sequence having at least 95% identity to the sequence of SEQ ID NO:15, and
   (xvi) a sequence having at least 95% identity to the sequence of SEQ ID NO:16.

2. A method of treating or preventing a human immunodeficiency virus (HIV) infection or a disease associated with an HIV infection in a subject in need thereof, comprising a prime-boost regimen of:
   (a) administering to the subject 1 to 10 administrations of a first viral vector encoding an immunogenic polypeptide as a prime, followed by;
   (b) administering to the subject 1 to 10 administrations of a second viral vector encoding the immunogenic polypeptide as a boost;
   wherein the immunogenic polypeptide comprises:
   (i) a sequence having at least 95% identity to the sequence of SEQ ID NO:1,
   (ii) a sequence having at least 95% identity to the sequence of SEQ ID NO:2,
   (iii) a sequence having at least 95% identity to the sequence of SEQ ID NO:3,
   (iv) a sequence having at least 95% identity to the sequence of SEQ ID NO:4,
   (v) a sequence having at least 95% identity to the sequence of SEQ ID NO:5,
   (vi) a sequence having at least 95% identity to the sequence of SEQ ID NO:6,
   (vii) a sequence having at least 95% identity to the sequence of SEQ ID NO:7,
   (viii) a sequence having at least 95% identity to the sequence of SEQ ID NO:8,
   (ix) a sequence having at least 95% identity to the sequence of SEQ ID NO:9,
   (x) a sequence having at least 95% identity to the sequence of SEQ ID NO:10,
   (xi) a sequence having at least 95% identity to the sequence of SEQ ID NO:11,
   (xii) a sequence having at least 95% identity to the sequence of SEQ ID NO:12,
   (xiii) a sequence having at least 95% identity to the sequence of SEQ ID NO:13,
   (xiv) a sequence having at least 95% identity to the sequence of SEQ ID NO:14,
   (xv) a sequence having at least 95% identity to the sequence of SEQ ID NO:15, and
   (xvi) a sequence having at least 95% identity to the sequence of SEQ ID NO:16.

3. The method of claim 1, wherein at least two of the sequences (i)-(xvi) are joined by a single, dual, or triple alanine amino acid linker, wherein the linker results in the formation of an AAA sequence in the junction region between adjoining sequences.

4. The method of claim 1, wherein the sequence of each of (i) to (xvi) is 11-85 amino acids in length.

5. The method of claim 1, wherein (a) comprises administering to the subject 1 to 4 administrations of the first viral vector encoding the immunogenic polypeptide, and/or (b) comprises administering to the subject 1 to 4 administrations of the second viral vector encoding the immunogenic polypeptide.

6. The method of claim 1, wherein (a) comprises administering to the subject one administration of the first viral vector encoding the immunogenic polypeptide, and (b)

comprises administering to the subject one administration of the second viral vector encoding the immunogenic polypeptide.

7. The method of claim 1, wherein the first viral vector is chimpanzee adenovirus (ChAd) vector and the second viral vector is a Modified Vaccinia Ankara (MVA) vector.

8. The method of claim 7, wherein the chimpanzee adenovirus vector is ChAdOx1.HTI and the Modified Vaccinia Ankara (MVA) virus vector is MVA.HTI.

9. A method for inducing an immune response against a human immunodeficiency virus (HIV) in a subject in need thereof, the method consisting essentially of a prime-boost regimen of:
(a) administering to the subject 1 to 5 administrations of a first viral vector encoding the immunogenic polypeptide as a prime, followed by;
(b) administering to the subject 1 to 5 administrations of a second viral vector encoding the immunogenic polypeptide as a boost;
wherein the immunogenic polypeptide comprises:
(i) a sequence having at least 95% identity to the sequence of SEQ ID NO:1,
(ii) a sequence having at least 95% identity to the sequence of SEQ ID NO:2,
(iii) a sequence having at least 95% identity to the sequence of SEQ ID NO:3,
(iv) a sequence having at least 95% identity to the sequence of SEQ ID NO:4,
(v) a sequence having at least 95% identity to the sequence of SEQ ID NO:5,
(vi) a sequence having at least 95% identity to the sequence of SEQ ID NO:6,
(vii) a sequence having at least 95% identity to the sequence of SEQ ID NO:7,
(viii) a sequence having at least 95% identity to the sequence of SEQ ID NO:8,
(ix) a sequence having at least 95% identity to the sequence of SEQ ID NO:9,
(x) a sequence having at least 95% identity to the sequence of SEQ ID NO:10,
(xi) a sequence having at least 95% identity to the sequence of SEQ ID NO:11,
(xii) a sequence having at least 95% identity to the sequence of SEQ ID NO:12,
(xiii) a sequence having at least 95% identity to the sequence of SEQ ID NO:13,
(xiv) a sequence having at least 95% identity to the sequence of SEQ ID NO:14,
(xv) a sequence having at least 95% identity to the sequence of SEQ ID NO:15, and
(xvi) a sequence having at least 95% identity to the sequence of SEQ ID NO:16.

10. The method of claim 9, wherein (a) comprises administering to the subject a single administration of the first viral vector encoding the immunogenic and/or (b) comprises administering to the subject a single administration of the second viral vector encoding the immunogenic polypeptide.

11. The method of claim 9, wherein the first viral vector is a ChAd vector and/or the second viral vector is an MVA vector.

12. The method of claim 1, wherein the first viral vector is administered at a dose of from about $1\times10^8$ to about $1\times10^{11}$ viral particles (vp).

13. The method of claim 12, wherein the first vector is administered at a dose of about $5\times10^{10}$ vp.

14. The method of claim 1, wherein the second viral vector is administered at a dose of about $1\times10^6$ to about $1\times10^{10}$ plaque forming units (pfu).

15. The method of claim 14, wherein the second viral vector is administered at a dose of about $2\times10^8$ pfu.

16. The method of claim 1, wherein the administration of the first viral vector and the administration of the second viral vector is separated by a period of about two weeks to about 24 weeks.

17. The method of claim 16, wherein the period between the administration of the first viral vector and the administration of the second viral vector is about 8 weeks.

18. The method of claim 1, wherein the immunogenic polypeptide further comprises a signal peptide at the N-terminus of the immunogenic polypeptide.

19. The method of claim 1, wherein the immunogenic polypeptide comprises the sequence of SEQ ID NO:99 or wherein the immunogenic polypeptide is encoded by a nucleic acid comprising SEQ ID NO:100 or 101.

20. The method of claim 2, wherein the disease associated with an HIV infection is an acquired immune deficiency syndrome (AIDS), AIDS-related complex (ARC), or HIV opportunistic disease.

21. The method of claim 20, wherein the HIV is HIV type 1 (HIV-1) or HIV type 2 (HIV-2).

22. The method of claim 1, wherein the subject is a human subject.

23. The method of claim 1, wherein the first viral vector is administered in a pharmaceutical composition comprising L-Histidine: 10 mM; NaCl: 35 mM; Sucrose: 7.5% (w/v); MgCl$_2$: 1 mM; EDTA disodium: 0.1 mM; Tween 80 (Polysorbate-80): 0.1% (w/v); Ethanol: 0.5% (v/v); HCl: Adjusted to pH 6.6, and/or the second viral vector is administered in a pharmaceutical composition comprising 0.5 mL Tris buffer (10 mM Tris HCl, pH 7.7, 140 mM NaCl).

24. The method of claim 2, wherein the method of treating or preventing a HIV infection comprises achieving virologic suppression in the subject.

25. The method of claim 2, wherein the method of treating or preventing a HIV infection comprises maintaining virologic suppression in the subject.

26. The method of claim 1, wherein the method further comprises administering to the subject one or more other anti-HIV therapies in conjunction with the first and second viral vectors encoding the immunogenic polypeptide.

27. The method according to claim 26, wherein said one or more anti-HIV therapies are administered sequentially or concurrently with the first and second viral vectors encoding the immunogenic polypeptide.

28. The method of claim 1, wherein the method treats or prevents a human immunodeficiency virus (HIV) infection or a disease associated with an HIV infection in the subject.

29. The method of claim 28, wherein the disease associated with an HIV infection is an acquired immune deficiency syndrome (AIDS), AIDS-related complex (ARC), or HIV opportunistic disease.

30. The method of claim 29, wherein the HIV is HIV type 1 (HIV-1) or HIV type 2 (HIV-2).

31. The method of claim 28, wherein the method comprises achieving virologic suppression in the subject.

32. The method of claim 28, wherein the method of treating or preventing a HIV infection comprises maintaining virologic suppression in the subject.

* * * * *